US 6,690,958 B1

(12) United States Patent
Walker et al.

(10) Patent No.: US 6,690,958 B1
(45) Date of Patent: Feb. 10, 2004

(54) ULTRASOUND-GUIDED NEAR INFRARED SPECTROPHOTOMETER

(75) Inventors: Stephen D. Walker, Boulder, CO (US);
Peter E. Nelson, Longmont, CO (US);
R. Dale Zellers, Lafayette, CO (US)

(73) Assignee: Nostix LLC, Boulder, CO (US)

( * ) Notice: Subject to any disclaimer, the term of this patent is extended or adjusted under 35 U.S.C. 154(b) by 37 days.

(21) Appl. No.: 10/143,248

(22) Filed: May 7, 2002

(51) Int. Cl.[7] .................................................. A61B 5/00
(52) U.S. Cl. ..................... 600/323; 600/338; 600/407; 600/309
(58) Field of Search ................. 600/309–310, 600/322–324, 473, 476, 437, 407, 313, 338

(56) References Cited

U.S. PATENT DOCUMENTS

| 4,697,593 A | * | 10/1987 | Evans et al. ............... 600/343 |
| 6,264,610 B1 | * | 7/2001 | Zhu .......................... 600/443 |
| 2002/0002372 A1 | * | 1/2002 | Jahns et al. ................ 606/41 |

FOREIGN PATENT DOCUMENTS

| GB | 2235288 A | * | 2/1991 | .......... G01N/21/31 |
| JP | 04-307042 | * | 10/1992 | ............ A61B/8/12 |

* cited by examiner

Primary Examiner—Max F. Hindenburg
Assistant Examiner—Matthew Kremer
(74) Attorney, Agent, or Firm—Ken J. Koestner

(57) ABSTRACT

A diagnostic apparatus includes a near infrared spectrophotometer (NIRS) and an ultrasound transducer that operate in combination to improve diagnostic measurements. The diagnostic apparatus includes a near infrared spectrophotometer that measures an analyte, for example tissue oxygenation, in an optical sample volume and an ultrasound imager to accurately position the optical sample volume in biological tissue or vessels. In one example, the diagnostic apparatus includes an optical source, a linear array of ultrasound transducers, and an optical photodetector arranged in the same plane so that the ultrasound sample volume interrogated by the ultrasound transducers intersects the optical sample volume formed by the optical source and detector.

25 Claims, 13 Drawing Sheets

ULTRASOUND-GUIDED NEAR INFRARED SPECTROPHOTOMETER

BACKGROUND OF THE INVENTION

1. Field of the Invention

The invention relates generally to physiological test devices and associated test methods and, more particularly, to test devices and methods that utilize near infrared spectrometry and ultrasound in combination.

2. Relevant Background

Subnormal blood oxygenation arises in many medical conditions.

Fetal hypoxemia is the subnormal oxygenation of arterial blood, an example of a low oxygenation condition, and results from a variety of disorders. Korst LM, Phelan JP, et al., "Acute fetal asphyxia and permanent brain injury: a retrospective analysis of current indicators", in *J. Matern-Fetal Med.* 1999; 8:275–288, studied 47 brain-injured infants and determined that fetal hypoxemia resulted from causes as follows: 14 (30%)-uterine rupture; 5 (11%)-shoulder dystocia; 5 (11%) cord prolapse; 3 (6%)-maternal cardiac arrest; 2 (4%)-placental abruption; 1 (2%)-fetal exsanguinations; and 17 (36%)-unknown. Fetal hypoxemia may cause infant mortality, fetal death, low birth weight, and severe mental retardation.

As oxygen levels begin to decline, the fetus can respond using one or more of several compensatory mechanisms to maintain an intracellular steady state. An increase in fetal heart rate can slightly increase cardiac output, as described by Thornburg KL, Morton MJ, "Development of the cardiovascular system", in: *Textbook of Fetal Physiology* (Thornburn G, Harding R, eds.), 1994, pp. 118–120, New York: Oxford University Press.

Where blood supply is reduced, the fetal circulatory system shunts the blood supply to vital organs such as the heart, brain, and adrenal glands to supply sufficient oxygen, as described by Peeters LL, Sheldon RD, Jones MD, et al., "Blood flow to fetal organs as a function of arterial oxygen content" in *Am J Obstet Gynecol* 1979;135:637–645.

In case of hypoxemia, the fetus enters a state of anaerobic metabolism. Anaerobic metabolism produces 18 times less energy than is produced under aerobic conditions, negatively impacting the fetus. (Nordstrom L, and Arulkumaran S, "Intrapartum Fetal Hypoxia and Biochemical Markers: A Review" in *Obstetrical and Gynecological Survey,* 1998;53:10, pp.645–657). Neuronal loss due to hypoxemia occurs in two phases. A primary loss takes place at the time of the hypoxic event, and a secondary loss occurs during a reoxygenation/reperfusion phase, hours to days after the event. (Pulsinelli W, Brierly J, and Plum F, "Temporal profile of neuronal damage in a model of transient forebrain ischemia" in *Ann Neurol* 1982; 11:491–498). The primary damage is due to deterioration of the cellular steady state including acidosis, disrupted ion distributions, and altered tissue perfusion. The damaging mechanisms of the secondary phase are metabolic changes, neurotoxicity, and circulatory changes.

Hypoxia occurs when the oxygen supply to the brain is inadequate for normal cellular function. Hypoxia can result in brain damage and/or death of the fetus. In-utero fetal hypoxia can result if the umbilical cord wraps around a fetus' neck, thereby restricting blood flow to the head. A high-risk fetus typically lacks cerebral blood pressure regulation mechanisms that are found in adults and normal fetuses. Contractions can cause cerebral hemorrhage that lead to hypoxia in a high-risk fetus.

Technological advances such as electronic fetal monitoring and fetal oximetry have failed to reduce fetal morbidity and mortality rates. Electronic fetal monitors (EFM) use acoustic energy to record the fetal heart rate. Cardiac accelerations and decelerations on the recording are visually analyzed to determine whether the fetus is in a distress condition. EFM was introduced into labor and delivery practice decades ago and has gained widespread use despite limited effectiveness. Studies of the efficacy of EFM have produced mixed results, concluding in many cases a poor correlation with fetal outcome.

A more recent technological advance is the development of fetal oximetry. Fetal oximeters use an optical source and photodetector attached directly to the fetal head. While fetal oximetry may assist an obstetrician in assessing fetal status, usage of oximeter technology requires rupture of maternal membranes, limiting oximetry usage to later stages of labor.

SUMMARY OF THE INVENTION

A diagnostic apparatus includes a near infrared spectrophotometer and an ultrasound transducer that operate in combination to improve diagnostic measurements.

In one aspect, the need for a method to precisely position the NIRS optical sample volume in tissue is met by ultrasound guided near infrared spectrometry.

In another aspect, a catheter includes optical sources, a photodetector, ultrasound transducer array, and stabilization balloon. The display shows an optical sample volume through tissue of interest that is superimposed over the ultrasound image, and an oxygenation indicator.

In another aspect, the diagnostic apparatus includes a near infrared spectrophotometer that measures tissue oxygenation in an optical sample volume and an ultrasound imager to accurately position the optical sample volume in biological tissue or vessels.

In one embodiment, the diagnostic apparatus includes an optical source, a linear array of ultrasound transducers, and an optical photodetector arranged in the same plane so that the ultrasound sample volume interrogated by the ultrasound transducers intersects the optical sample volume formed by the optical source and detector.

In some embodiments, the optical source and photodetector are attached to rotary and linear sensors that supply position data, for example to processing element such as a computer, processor, controller, logic element, or the like. The processing element can calculate the distance between the optical source and the photodetector. The source-detector distance and tissue optical properties based on near infrared spectrophotometer measurements determine the position of the optical sample volume in the tissue. Calibration fixtures or phantoms that have optical properties similar to the tissue of interest can be used to determine the shape of the optical sample volume for a particular source-detector distance.

In another aspect, some systems may include an electronic graphics display and a processing or control element that superimposes an experimentally-determined optical sample volume over an ultrasound image on the display. The combined optical sample volume and ultrasound image display enables a clinician to use the electronic display to accurately position the optical sample volume through a desired tissue portion.

In operational aspects, the diagnostic apparatus is capable of performing a noninvasive method of precisely positioning a optical sample volume projected and received by a near infrared spectrophotometer (NIRS) in deep tissue through usage of an ultrasound imager. An example of the positioning method includes several actions such as arranging an optical source, a linear array of ultrasound transducers, and an optical photodetector in the one plane so that the ultrasound sample volume intersects the optical sample volume. An outline of the theoretical optical sample volume is superimposed over the ultrasound image on an electronic graphics display. The superimposed image on the electronic graphics display enables or facilitates the capability of a clinician to accurately position the optical sample volume through the desired tissue.

Various embodiments and examples of the diagnostic apparatus can be used for different tasks. A tissue analysis device, for example capable of taking measurements through the skin, can be used for functions such as noninvasive detection of fetal hypoxemia. A catheter device can be used for functions such as noninvasive determination of oxygenation level in tissue through vessels and body openings including but not limited to oral, rectal, nasal, and otic openings. For example a catheter may be used to establish whether oxygenation is sufficient for the heart to be successfully resuscitated by defibrillation.

BRIEF DESCRIPTION OF THE DRAWINGS

The features of the described embodiments believed to be novel are specifically set forth in the appended claims. However, embodiments of the invention relating to both structure and method of operation, may best be understood by referring to the following description and accompanying drawings.

DESCRIPTION OF THE EMBODIMENT(S)

Near infrared spectrophotometry measurements are used in medical, biological, and physiological devices to measure the concentration of light-absorbing analytes in human tissue.

Figure 1A:
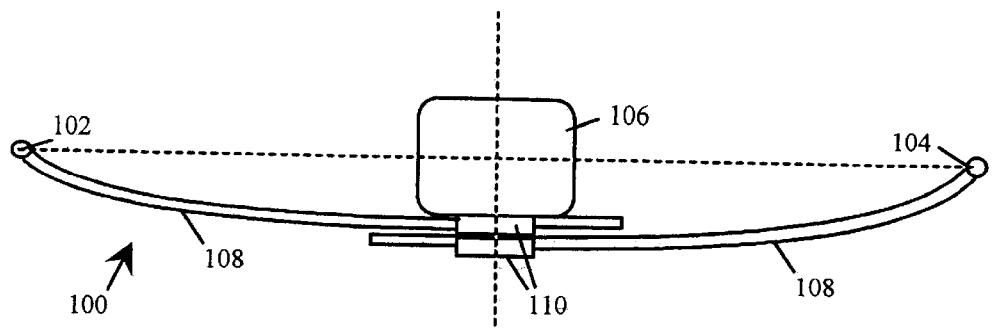
FIGS. 1A and 1B are schematic pictorial diagrams that illustrate respective side and top views of an example of a combined optical-acoustic diagnostic apparatus in a trans-abdominal fetal oxygenation probe configuration.
Figure 1B:
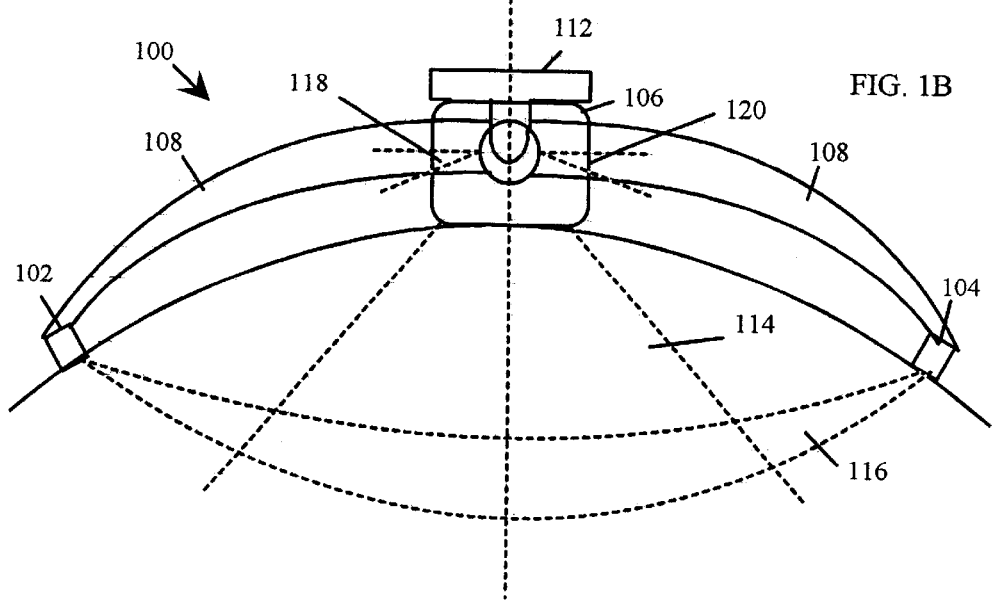

Referring to FIGS. 1A and 1B, pictorial diagrams illustrate respective side and top views of an example of a combined optical-acoustic diagnostic apparatus 100 in a trans-abdominal fetal oxygenation probe configuration. The illustrative trans-abdominal fetal oxygenation probe 100 includes an optical source 102 and detector 104, and an ultrasound transducer 106. The optical source 102 and the detector 104 are connected to one or more lateral members 108 or arms that separate the optical source 102 and detector 104. The optical source 102 generates an optical light signal that passes through a medium, for example a tissue sample, interposed between the optical source 102 and detector 104, and is detected by the detector 104. The optical sample volume is the tissue illuminated by the detected optical light signal.

In the illustrative example of the optical-acoustic diagnostic apparatus 100, the lateral members 108 are rigid arms constructed from any material with suitable mechanical characteristics such as strength, rigidity, weight for supporting and holding the optical source 102 and detector 104. The lateral members 108 are also connected to the ultrasound transducer 106 that generates acoustic signals for transmission as ultrasonic pressure waves into tissue, and receives returning echoes from the tissue. The lateral members 108 and the ultrasound transducer 106 connect in a configuration that aligns the optical sample volume to intersect the ultrasound sample volume. In the illustrative example, a bracket 112 couples the ultrasound transducer 106 to the lateral members 108 although any suitable connector can be used. In some embodiments, position sensors 110 are coupled to the lateral members 108, for example to facilitate alignment of the optical sample volume and the ultrasound sample volume. In the illustrative example, the position sensors 110 include rotary and linear position sensors that are connected to the ultrasound transducer 106 and the lateral members 108.

Any suitable optical source 102 can be used. In some embodiments, the optical source 102 can be formed from semiconductor laser diodes, permitting a relatively low-cost sensor.

The ultrasound transducer 106 typically includes a plurality of transducer elements arranged in an array, and may be of any suitable transducer type including a linear array, a phased linear array, a phased array, an annular array, or the like.

FIG. 1B depicts the optical-acoustic diagnostic apparatus 100 in usage for trans-abdominal fetal imaging with the ultrasound transducer 106, the optical source 102, and the detector 104 in contact with maternal abdominal skin. The ultrasound transducer 106 interrogates a ultrasound sample volume 114 that typically has a trapezoidal shape. The optical source 102 and detector 104 generate an optical sample volume 116. The arrangement of the optical source 102, the detector 104, and the ultrasound transducer 106 in a same linear plane aligns the optical sample volume 116 to intersect the ultrasound sample volume 114.

The position sensors 110 detect the adjustable configuration of the ultrasound transducer 106, and the lateral members 108 connected to the optical source 102 and the detector 104, for example at an axle, pin, axis, pivot, or the like for pivotal relative motion of the lateral members 108. Rotary and linear position sensors 110 detect, for example, a source angle 118 and a detector angle 120. The source angle 118 relates to the angle between the ultrasound transducer 106 and the lateral member 108 holding the optical source 102. The detector angle 120 relates to the angle between the ultrasound transducer 106 and the lateral member 108 holding the optical detector 104. The source angle 118 and detector angle 120 can be used using simple geometric relations, for example by a processor, to determine a source-detector distance, based on the known length of the lateral members 108. A suitable processor may be a control circuit, a microprocessor, a microcontroller, a logic circuit, a programmable device logic, or the like.

In various embodiments, an optical-acoustic diagnostic apparatus generally has one or more of several characteristics that promote safety and effectiveness over other diagnostic devices and procedures. For example, an optical-acoustic diagnostic apparatus is typically noninvasive and utilizes nonionizing energy. In many examples, the optical-acoustic diagnostic apparatus has a size and form factor that approximate characteristics of a diagnostic ultrasound imager, facilitating bedside utility. Typical embodiments can perform continuous tissue oxygenation measurements at rapid refresh rates, for example at rates that meet or exceed a patient's heart rate, a rate that has high clinical utility. The optical-acoustic diagnostic apparatus typically has high reliability since fragile fiber optic cables are not required for transmitting and receiving light.

Figure 2:
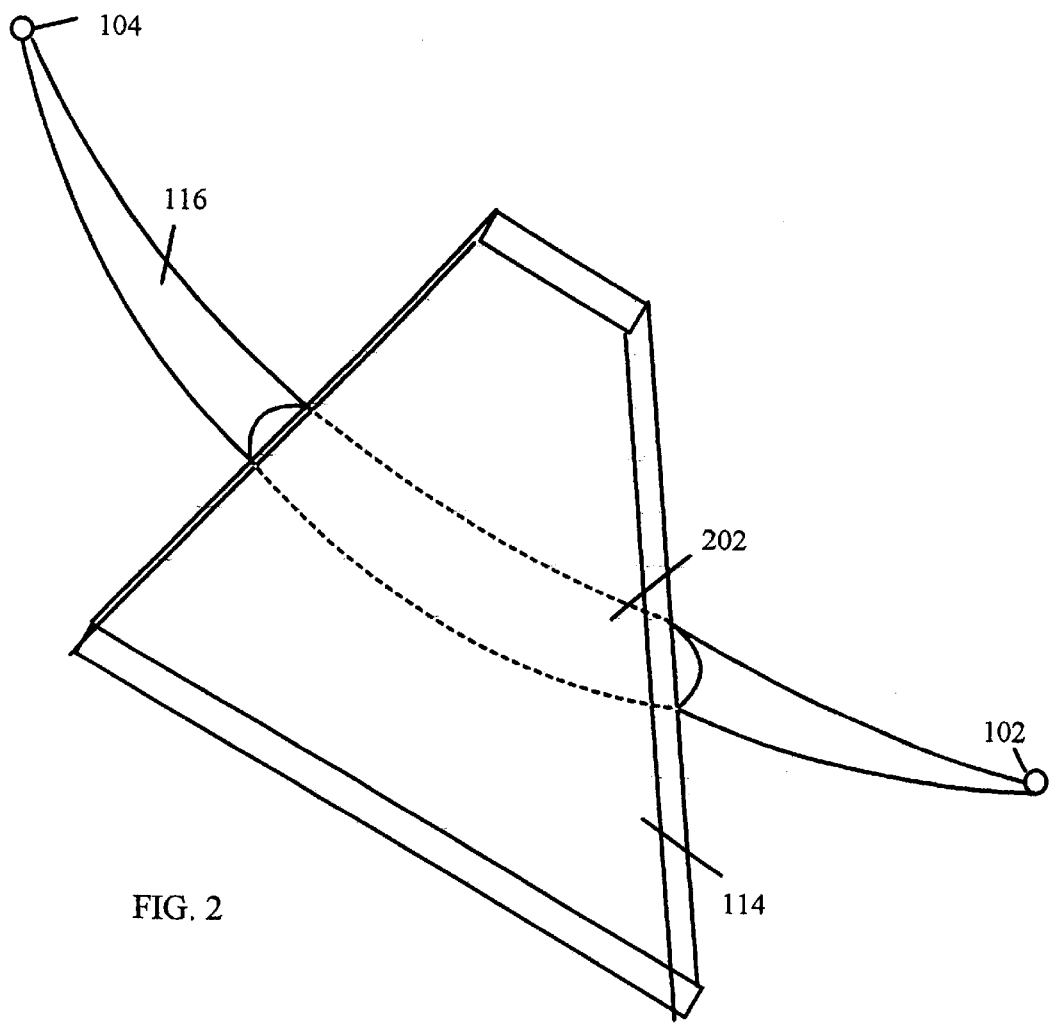
FIG. 2 is an example of a three-dimensional pictorial diagram showing tissue fields interrogated by optical and acoustic sensors in an optical-acoustic diagnostic apparatus including an optical sample volume intersected by an ultrasound sample volume.

Referring to FIG. 2, a three-dimensional pictorial diagram shows tissue fields interrogated by optical and acoustic sensors in an optical-acoustic diagnostic apparatus including an optical sample volume 116 intersected by an ultrasound sample volume 114. Typically, the ultrasound sample volume 114 is trapezoid shaped and has a thickness that approximates that of transducer elements in the ultrasound transducer 106. The optical sample volume 116 has a shape that approximates a thickened crescent, "crescent-moon" shape, or banana shape suspended on one end from the optical source 102 and on the other end from the photodetector 104. The optical sample volume 116 may have an approximately symmetric form or may have some asymmetry, depending generally on characteristics of the optical source 102, the detector 104, and tissue between the optical source 102 and detector 104.

The distance between the optical source 102 and the photodetector 104 determines the depth of the center 202 of the optical sample volume 116. The depth is equal to one-third of the source-detector distance. The optical sample volume center 202 moves deeper into tissue in response to lengthening the optical source-photodetector distance.

Ultrasound imaging can display deep tissue structures but generally does not generate functional information. Typically, an ultrasound transducer is positioned in contact with a patient's skin and is activated to emit a pulse of acoustic energy into the patient's tissue. The optical-acoustic diagnostic apparatus can display echoes from acoustic reflectors in the tissue as a two-dimensional image on a graphics display. Near infrared spectrophotometry can be used to obtain diagnostic or functional information from a tissue position identified using ultrasound imaging. Near infrared spectrophotometry involves measurement of tissue adsorption in an optical sample volume. The position of an optical sample volume can be determined by measurement of optical source-detector distance.

Figure 3:
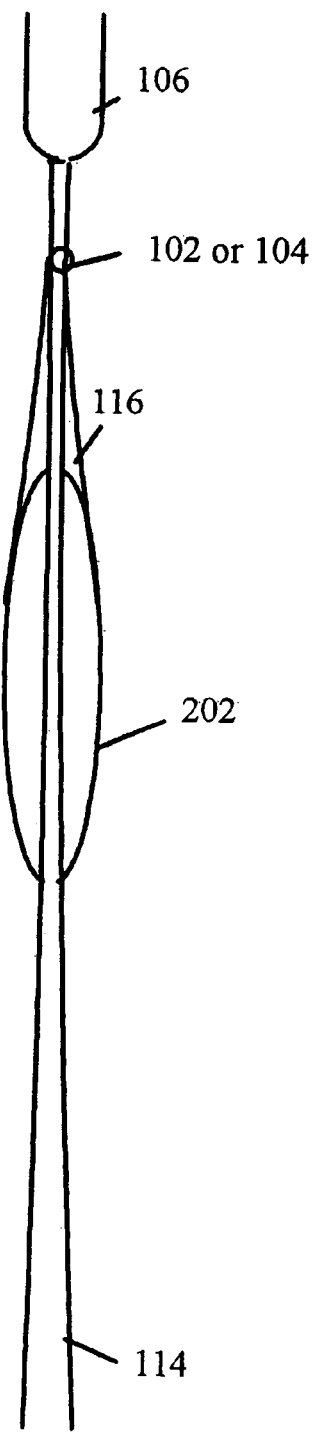
FIG. 3 is an example of a cross-sectional pictorial view illustrating an optical sample volume intersected by an ultrasound sample volume.

Referring to FIG. 3, a cross-sectional pictorial view illustrates one example of an optical sample volume 116 intersected by an ultrasound sample volume 114, approximately in the vicinity of the optical sample volume center 202. In the illustrative example, the optical sample volume has an approximately circular cross-sectional shape, but may vary in shape according to characteristics of the optical source and detector, and tissue. The ultrasound sample volume generally has widening but relatively constant field width in the field near the transducer, with more pronounced widening at further tissue depths. The form of the ultrasound sample volume cross-section varies depending focusing characteristics of the ultrasound transducer 106, the frequency of the ultrasound transducer 106, and tissue characteristics. Relative sizes of the optical sample volume and the ultrasound sample volume vary depending on the physical dimensions of the optical source 102 and detector 104, and elements of the ultrasound transducer 106, and characteristics of the tissue.

Oxyhemoglobin ($HbO_2$) and deoxyhemoglobin (Hb) concentrations in the optical sample volume 116 are measured by alternately passing narrow band near infrared light of different wavelengths between the optical source 102 and photodetector 104 according to a method of noninvasive optical sensing for measuring near infrared light absorbing analytes described herein.

Figure 4:
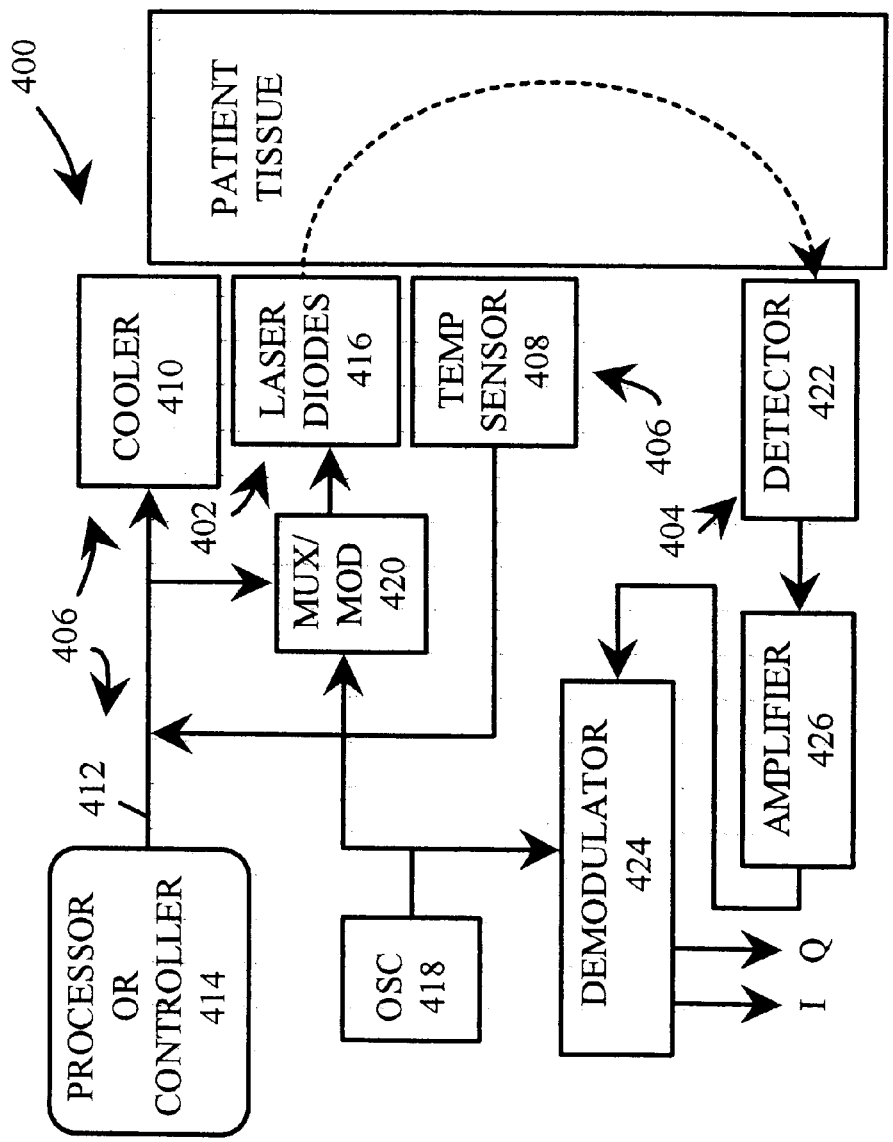
FIG. 4 depicts a schematic block diagram showing a near infrared spectrophotometer that is suitable for optical sampling and formation of the optical sample volume.

Referring to FIG. 4, a schematic diagram illustrates an example of a near infrared spectrophotometer 400. Fundamental elements of the near infrared spectrophotometer 400 are an optical radiation source 402 and a detector 404 for detecting radiation produced by the optical source 402. The illustrative near infrared spectrophotometer 400 has a single optical source 402 and a single detector 404 although additional sources and detectors may be utilized in other systems.

The near infrared spectrophotometer 400 also includes a temperature control system 406 including a temperature sensor 408 and a wavelength shifter 410. The near infrared spectrophotometer 400 has control interconnections 412 for controlling the optical source 402 and the temperature control system 406. The control interconnections 412 supply control signals from a controller 414 to the optical source 402 and wavelength shifter 410, and receive signals from the temperature sensor 408. In various embodiments, the controller 414 may be implemented in different forms such as a processor, a CPU, a microcontroller, a digital signal processor (DSP), logic circuits, programmable logic arrays, and the like. Some examples of the near infrared spectrophotometer 400 may include an internal controller 414 so that the control interconnections 412 may be a control line, a bus, or other internal interconnect. Other systems may have an external control system so that the control interconnections 412 may include an interface such as a serial interface, a parallel interface, an external bus interface or the like.

The controller 414, whether internal or external, may include other interconnections for interfacing to external devices, for example infusion pumps, electrophysiologic control devices, ventilators, and many other diagnostic and therapeutic devices. The near infrared spectrophotometer 400 may be used in combination with other clinical and laboratory techniques using the interface or without interfacing to improve the diagnosis, treatment, or prevention of a pathophysiologic condition.

The near infrared spectrophotometer 400 can utilize the controller 414 to monitor physiologic function of a patient. The controller 414 can execute processes that monitor physiologic parameters for early recognition of a condition and, upon detection of the condition, rapidly supply a suitable treatment for various conditions. For example, monitoring of a condition can be used to control automated administration of drugs to meet the patient's needs. Monitoring can be used to automatically reduce automated inspired oxygen levels to minimal levels of effective oxygenation for ventilated patients, reducing problems related to toxicity of excessive concentrations of oxygen.

In an illustrative system, the optical source 402 utilizes laser diodes 416 to generate optical radiation. The laser diodes 416 are activated by electrical signals from an oscillator 418 as controlled by a multiplexer/modulator 420. Other types of optical sources may be utilized in other embodiments. Suitable optical sources include vertical cavity surface emitting lasers (VCSEL), edge-emitting laser diodes, distributed feedback lasers (DFB), and the like. Typically a single optical source 402 is used although some systems may utilize multiple optical sources.

The detector 404 includes an optical detector 422 that detects optical signals and applies the optical signals to a demodulator 424. An amplifier 426 is positioned between the optical detector 422 and the demodulator 424 to amplify the signals. One example of a suitable amplifier 426 is a preamplifier followed in series by an amplifier.

The demodulator 424 produces In-Phase (I) and Quadrature (Q) measures of the detected signal. The oscillator 418 applies electrical signals to the demodulator 424.

The optical source 402 has several design characteristics that enhance the measurement of small absorbances and short path lengths in tissue. The optical source 402 generates infrared energy that irradiates tissue at wavelengths chosen to minimize water interference and to maximize the absorbance of a compound of interest. The entering wavelengths are further specified to be in a spectral region in which slight changes in wavelength produce significant changes in absorbance level of the analyte of interest. For example, 760 nm to 765 nm is an optical wavelength range for measuring absorption of oxyhemoglobin and deoxyhemoglobin as the compounds of interest. When the wavelength is shifted slightly from 760 nm to 765 nm the change in absorbance is significant.

The detector 404 has aspects that are exploited to accurately measure path length in tissue. The demodulator 424, amplifier 426, and optical detector 422 of the detector 404 are operated to accurately measure pathlength on the basis of modulation phase and amplitude shift measurements. Modulation phase shift increases with increasing path length and provides the basis for path length measurement.

The controller 414 controls the optical radiation source 402 and detector 404 to shift the incident wavelength to reduce or eliminate scattering error. The controller 414 controls the multiplexer 420 in the signal pathway from oscillator 418 to the laser diodes 416 to use wavelength shifting on the order of 2–5 nm to reduce scattering error. The near infrared spectrophotometer 400 acquires two measurements with an identical optical path. The light loss due to scattering is constant, the same in both measurements, so that a change in reflected light is mainly caused by absorbance of the selected analyte of interest.

In an illustrative embodiment, the modulator 420, VCSEL laser diodes 416, and wavelength shifter 410 are controlled through a digital port of controller 414, an embedded microcomputer. In one example, the laser diodes 416 are configured as two ten-element VCSEL arrays. Each VCSEL array element emits 1 mW to produce a total of 10 mW when all ten elements activated. The 10 mW value is ten percent of the recognized laser damage threshold of 100 mW. The controller 414 also monitors skin temperature with the temperature sensor 408 positioned in close proximity to the VCSELs of laser diodes 416. If skin temperature exceeds a predetermined threshold, the VCSELs are immediately inactivated.

In one example, the oscillator 418 generates a 125 MHz signal for both modulation and demodulation. Multiplexer 420 sequentially applies radio frequency modulation to each VCSEL in the laser diodes 416 so that only a single VCSEL is activated at any time.

The emitted wavelength is shifted either longer or shorter by the wavelength shifter 410. One or more of several possible techniques are used to shift wavelengths. One technique is to vary input current to the source. An increase in current lengthens the wavelength. Another technique is to control optical source temperature with a thermoelectric cooler. Higher temperatures result in longer wavelengths. Cooler temperatures produce shorter wavelengths. A third technique is to attach a tunable external cavity to the optical source.

Another class of techniques involves usage of microelectro-mechanical systems (MEMS) forming a portion of the optical source to vary wavelength of the optical source. Optical MEMS products, which may be called micro-opticoelectro-mechanical systems (MOEMS) typically operate by manipulating tiny mirrors within the optical source. Individuals having ordinary skill in the MEMS art are familiar with MEMS chips that use light beam-directing mirrors that move independently and nearly instantaneously during operation. A MEMS optical source can be arranged into pixels in which a pixel can be activated by directing a mirror at a projection lens and be deactivated by directing the mirror away from the projection lens.

Other classes of MEMS devices can shift the wavelength by altering the dimension of a cavity laser. In one example, a Littman cavity combines a high-power Fabry-Perot diode gain medium, a microlens, and a grating with a MEMS-adjustable external mirror. In another example, a rotating mirror tunes wavelength to allow a selected diffracted wavelength to couple back to the laser diode. In a further example, superposition of diode gain, grating dispersion, and external cavity modes controls lasing wavelegth. In another example, closed-loop servo control can be used to control mirror position to accurately stabilize laser wavelength. The illustrative MEMS techniques are known to those having ordinary skill in the MEMS and MOEMS arts.

Other suitable techniques for shifting wavelength that are known to one having ordinary skill in the art may also be used.

The wavelength shifter 410 first shifts the emitted wavelength to long values and In-Phase (I) and Quadrature (Q) results are measured. The wavelength shifter 410 then lowers the emitted wavelength to short values, and measurements are repeated. The measurements produce In-Phase (I) and Quadrature (Q) results that the controller 414 users to calculate modulation amplitude difference $dA/d\mu_a$ and phase difference $d\theta/d\mu_a$.

An optimum pathlength of about 60 mm generates about a 1 degree phase change in the measurement, or approximately 0.2 nsec for a 125 MHz source signal.

In one example, the optical detector 422 is an avalanche photo diode. A source/detector separation of 4 cm gives a mean penetration of 2 cm and a tissue volume of approximately 5 ml.

Typically, measurements can be made at a patient's bedside. A clinician places the optical source 402 and photodetector 404 over a body region of the patient at which measurements are desired. Near infrared light penetrates several centimeters into the tissue. A portion of the light is reflected back to the photodetector 404 on the skin. Wavelengths of the entering light are selected to emphasize the light absorbing compounds of interest. High frequency modulation of the light beam is used to determine path length and measure light absorbing compound concentration. Slight shifts in wavelength of the optical sources are used to eliminate interference from scattered light.

The near infrared spectrophotometer 400 measures the distribution of light absorbing compounds. The optical source 402 emits near infrared light through the scalp and skull into cerebral tissue. The path of photons that arrive at the detector is a wide arc due to the presence of scatterers in the cerebral tissue that alter the photon trajectory. The detector 404 measures reflected light, which is amplified by amplifier 426 and transmitted via the control interconnections 412 such as a cable.

Near infrared spectrophotometry quantifies the concentration of light absorbing analytes in cerebral tissue by measuring the magnitude of the optical absorption. The Beer-Lambert law states that the optical absorbance of an analyte is proportional to both the concentration of the analyte and the path length. Technical challenges include the difficulty in measuring relatively small absorbances and the difficulty of determining the true optical path length.

The concentration of absorbing analytes in tissue and blood is determined by near infrared spectrophotometry from the difference between the entering light and the reflected light. The differences are caused by light absorption in the analytes and the light scattering effect of tissue in the light path including, for example, scalp and skull as well as soft tissue. Light absorption is described by an absorption coefficient $\mu_a$. Light scattering effect is described by a scattering coefficient $\mu'_s$.

Several different techniques are implemented to ensure accurate measurements. In a first example, wavelengths are selected that reduce or effectively eliminate water interference. In a second example, modulation is used to determine path length. In a third example, a wavelength shift to the entering light is used to eliminate the error caused by the light scattering.

The near infrared spectrophotometer 400 operates at measurement wavelengths at which water does not interfere. Water absorption is weak within the wide 700–900 nm and narrow 1600–1620 nm ranges, allowing clear detection of compounds within the ranges. Light in the wavelength ranges is not absorbed by water and penetrates several centimeters into tissue.

The near infrared spectrophotometer 400 measures pathlength by producing an entering beam that is intensity modulated. The phase difference in modulation between the entering light and reflected light is a measure of path length. Phase θ and amplitude A of reflected beam RF modulation are determined with In-Phase (I) and Quadrature (Q) demodulation parameters, according to equations (1) and (2) as follows:

$$\theta = \tan^{-1}\left(\frac{Q_{dc}}{I_{dc}}\right) \qquad (1)$$

where the In-Phase (I) and Quadrature (Q) components are produced by the demodulator 424 and used to determine phase difference θ and amplitude A as a measurement of pathlength. In some embodiments, the near infrared spectrophotometer 400 utilizes a controller 414, either internal or external, to measure pathlength.

The near infrared spectrophotometer 400 reduces or eliminates scattering error by varying the entering light wavelength by a few nanometers and then repeating the measurement of the modulation parameters. A slightly different total absorption is obtained because the analyzed absorption coefficients are different for different wavelengths. The scattering coefficient $\mu'_s$, does not change significantly with slight wavelength shift and is therefore a constant. Changes in modulation intensity and phase between the entering and reflected light are related to the absorption coefficient $\mu_a$ by a linear function of c, the speed of light according to equation (3):

$$\mu_a = \frac{\ln 10}{-2c}\left(\frac{dA/d\mu_a}{d\theta/d\mu_a}\right) = \frac{\ln 10}{-2c}\left(\frac{\Delta A}{\Delta \theta}\right) \qquad (3)$$

where $dA/d\mu_a$ is the modulation amplitude difference and $d\theta/d\mu_a$ is the phase difference between two slightly shifted wavelengths.

Arterial Saturation Measurement

One clinical application of near infrared spectrophotometer 400 is measurement of tissue arterial saturation. The near infrared spectrophotometer 400 performs absorbance measurements at different wavelengths and uses the difference to determine arterial saturation. Saturation values are approximately linearly related to the difference in absorbance values. One or more laser diodes 416 perform measurements at a suitable range of wavelengths. One appropriate wavelength range for arterial saturation measurements using a single laser diode is a range from 795 nn to 805 nm, although other ranges are possible. For the wavelength range from 795 mn to 805 nn, oxyhemoglobin ($HbO_2$) absorbance has a moderate positive slope of +0.01 $cm^{-1}$/nm and deoxyhemoglobin (Hb) absorbance has a negative slope of –0.005 $cm^{-1}$/nm.

Blood Flow Measurement

Another clinical application of near infrared spectrophotometer 400 is measurement of blood flow, such as cerebral blood flow. The near infrared spectrophotometer 400 accurately measures absorption and determines concentration of deoxyhemoglobin (Hb) and oxyhemoglobin ($HbO_2$) in a selected region of the body. In one example, deoxyhemoglobin and oxyhemoglobin concentration is determined in a selected region of the brain. Cerebral blood flow is the amount of blood passing through a volume of brain tissue and is suitably estimated as the difference between oxygen arrival rate and departure rate from the brain. One accurate estimate of cerebral blood flow is the difference in oxyhemoglobin and deoxyhemoglobin concentrations in the brain, the concentration difference [$HbO_2$]–[Hb].

The near infrared spectrophotometer 400 calculates oxyhemoglobin and deoxyhemoglobin concentrations based on the oxyhemoglobin and deoxyhemoglobin absorption measurements obtained at different wavelengths. In one example of a measurement system, selected wavelengths are 760 nm and 800 nm. At 760 nm, deoxyhemoglobin (Hb) absorption is dominant at a level of approximately 0.08 cm$^{-1}$ in comparison to the oxyhemoglobin (HbO$_2$) absorption of about 0.03 cm$^-$. At 800 nm, oxyhemoglobin (HbO$_2$) absorbance has a positive slope and deoxyhemoglobin (Hb) absorbance has a negative slope. Other wavelengths may be suitable.

In the illustrative embodiment, the near infrared spectrophotometer 400 utilizes controller 414 to perform calculations for solving the two equations for absorption coefficients $\mu_a$ determined at the two wavelengths. The two equations are solved to determine deoxyhemoglobin and oxyhemoglobin concentrations [Hb] and [HbO$_2$], respectively, in equations (4) and (5), as follows:

$$\mu_a^{760} = \epsilon_{Hb}^{760} \cdot [Hb] + \epsilon_{HbO2}^{760} \cdot [HbO_2] \tag{4}$$

and $$\mu_a^{800} = \epsilon_{Hb}^{800} \cdot [Hb] + \epsilon_{HbO2}^{800} \cdot [HbO_2] \tag{5}$$

where $\epsilon$ are hemoglobin absorption coefficients that are known physical parameters that are specified at various wavelengths included the measurement wavelengths of 760 nm and 800 nm.

The calculation of blood flow is made according to the Fick principle, which states that blood flow, is equal to the metabolic oxygen consumption rate divided by the difference between arterial oxygen and venous oxygen according to equation (6).

$$BloodFlow(ml_{blood}/\min) = \frac{O_2 uptake(umol/\min)}{(ArterialO_2 - VenousO_2)(umol/mlblood)}. \tag{6}$$

If oxygen uptake and arterial oxygen are constant, then changes in blood flow produce decreases in venous oxygen. The concentration difference, [HbO$_2$]–[Hb] is highly sensitive to changes in venous oxygen because venous blood makes up approximately 80% of the total cerebral blood volume. Blood flow in a sample volume is determined as the difference between oxyhemoglobin (HbO$_2$) and deoxyhemoglobin (Hb) concentrations according to equation (7), as follows:

$$\text{Blood Flow} = k([HbO_2]-[Hb]) \tag{7}$$

where k is a constant with units of ml$_{blood}$/min/$\mu$mol.

Serum Ferritin Measurement

Another area of clinical utility for near infrared spectrophotometer 400 is measurement of serum ferritin, a predictor of the acute respiratory distress syndrome (ARDS), a diffuse non-cardiogenic lung edema.

The near infrared spectrophotometer 400 can measure serum ferritin, typically using controller 414 to perform calculations for solving three equations for absorption coefficients $\mu_a$ determined at three wavelengths. Absorption coefficients $\mu_a$ are determined at three wavelengths, for example 760 nm to determine deoxyhemoglobin [Hb] concentration, 800 nm to determine oxyhemoglobin [HbO$_2$] concentration and 850 nm to determine ferritin [Fe+3] concentration. Three equations are solved to determine deoxyhemoglobin, oxyhemoglobin, and ferritin concentrations [Hb], [HbO$_2$], and [Fe+3] concentrations, respectively, in equations (8), (9), and (10), as follows:

$$\mu_a^{760} = \epsilon_{Hb}^{760} \cdot [Hb] + \epsilon_{HbO2}^{760} \cdot [HbO_2] + \epsilon_{Fe+3}^{760} \cdot [Fe+3] \tag{8}$$

$$\mu_a^{800} = \epsilon_{Hb}^{800} \cdot [Hb] + \epsilon_{HbO2}^{800} \cdot [HbO_2] + \epsilon_{Fe+3}^{800} \cdot [Fe+3] \tag{9}$$

and $$\mu_a^{850} = \epsilon_{Hb}^{850} \cdot [Hb] + \epsilon_{HbO2}^{850} \cdot [HbO_2] + \epsilon_{Fe+2}^{850} \cdot [Fe+3] \tag{10}$$

where $\epsilon$ are hemoglobin and ferritin absorption coefficients that are known physical parameters that are specified at various wavelengths included the measurement wavelengths of 760 nm, 800 nm, and 850 nm.

The near infrared spectrophotometer 400 can be used to noninvasively measure ferritin with or without iron-binding proteins.

Tissue Blood Gas Measurement

An additional area of clinical utility of the near infrared spectrophotometer 400 is measurement of parameters such as partial pressure of oxygen (PaO$_2$), partial pressure of carbon dioxide (PaCO$_2$), and pH in tissue. The near infrared spectrophotometer 400 is capable of measuring PaCO$_2$, PaO$_2$, and pH noninvasively, for example by using controller 414 to perform calculations for solving three equations for absorption coefficients $\mu_a$ determined at three wavelengths. Absorption coefficients $\mu_a$ are determined at three wavelengths, for example 760 nm to determine deoxyhemoglobin [Hb] concentration, 800 nm to determine oxyhemoglobin [HbO$_2$] concentration, and 1620 nm to determine carbon dioxide [CO$_2$] concentration. Three equations are solved to determine deoxyhemoglobin, oxyhemoglobin, and carbon dioxide concentrations [Hb], [HbO$_2$], and [CO$_2$] concentrations, respectively, in equations (11), (12), and (13), as follows:

$$\mu_a^{760} = \epsilon_{Hb}^{760} \cdot [Hb] + \epsilon_{HbO2}^{760} \cdot [HbO_2] + \epsilon_{CO2}^{760} \cdot [CO_2] \tag{11}$$

$$\mu_a^{800} = \epsilon_{Hb}^{800} \cdot [Hb] + \epsilon_{HbO2}^{800} \cdot [HbO_2] + \epsilon_{CO2}^{800} \cdot [CO_2] \tag{12}$$

and $$\mu_a^{1620} = \epsilon_{Hb}^{1620} \cdot [Hb] + \epsilon_{HbO2}^{1620} \cdot [HbO_2] + \epsilon_{CO2}^{1620} \cdot [CO_2] \tag{13}$$

where $\epsilon$ are hemoglobin and carbon dioxide absorption coefficients that are known physical parameters that are specified at various wavelengths included the measurement wavelengths of 760 nm, 800 nm, and 1620 nm.

Figure 5:
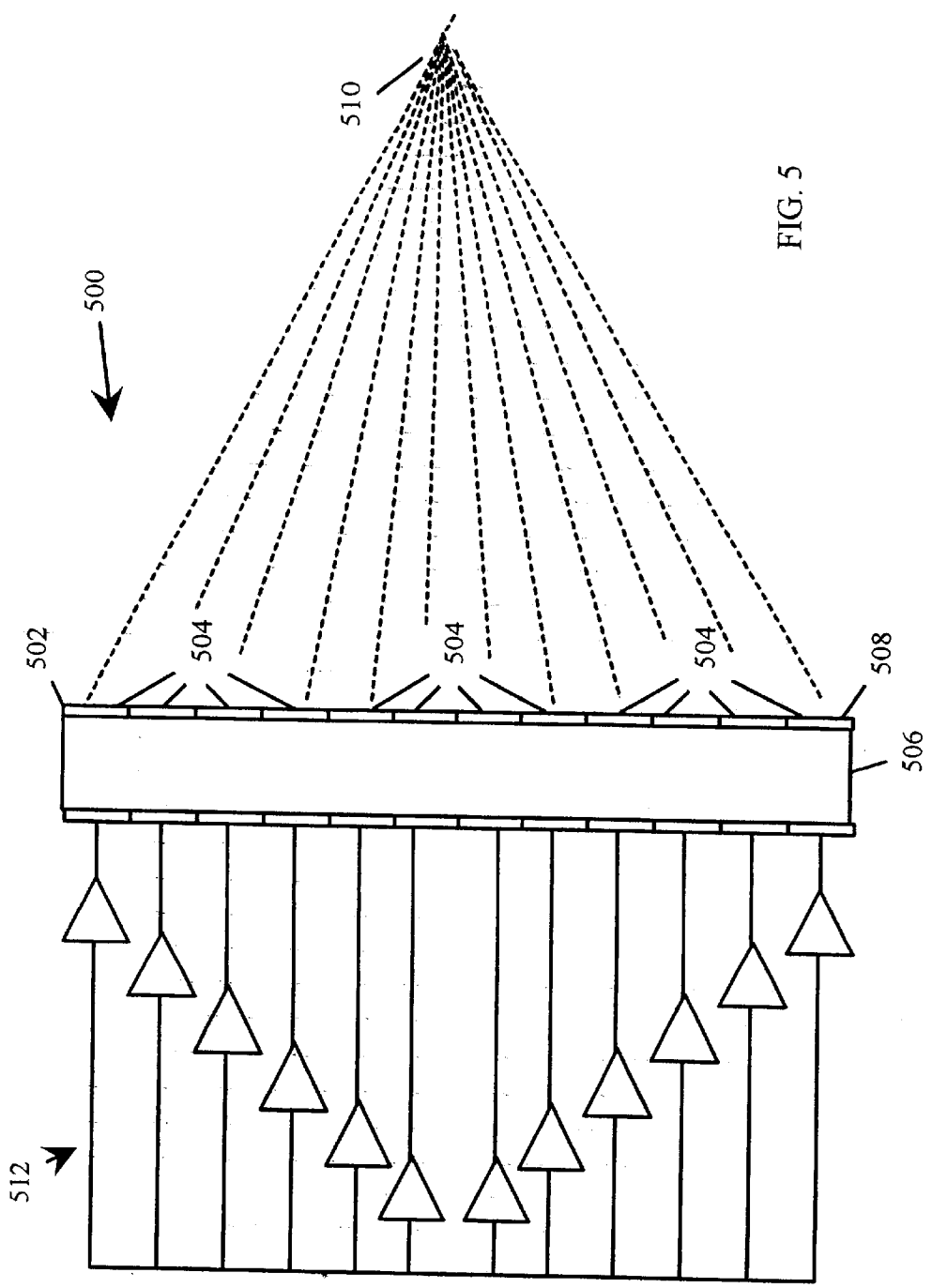
FIG. 5 is a schematic block diagram showing an acoustic array architecture that is suitable for usage in an optical-acoustic diagnostic apparatus.

Referring to FIG. 5, a schematic block diagram shows an acoustic array architecture 500 that is suitable for usage in an optical-acoustic diagnostic apparatus 100. One illustrative ultrasound transducer 106 is a linear ultrasound array 502 with multiple ultrasound transducer elements 504. The ultrasound transducer elements 504 are mounted on an ultrasound transducer support 506. The linear ultrasound array 502 has a plurality of ultrasound transducer elements 504, typically in the form of piezoelectric (PZT) wideband crystals. The ultrasound transducer elements 504 extend through the ultrasound transducer support 506 and extend to a body interface surface 508 so that ultrasound transducer elements 504 transmit ultrasound waves outward from the body interface surface 508 into tissue.

In the illustrative example, the ultrasound transducer elements 504 are arranged in a linear matrix that produces a field of view by multiple acoustic lines propagated normal to the face of the linear ultrasound array 502. A delay circuit 512 generates extensions of the normal acoustic lines pass through a common center of curvature 510. The linear ultrasound array 502 can be configured in a planar form, curved form, or other suitable form to produce a desired ultrasound sample volume. In one example, the field of view for a curved linear transducer array can be expanded by a set of acoustic lines propagated at varying angles to the face of the curved linear array. Various shapes, forms, and configurations of linear arrays are well known in the art of ultrasound imaging. Various ultrasound focusing techniques are well known for suitably forming a ultrasound sample volume.

Other types of ultrasound transducers may be alternatively used. For example, suitable ultrasound transducer 106 configurations include two-dimensional arrays of various forms including matrices of circular, square, oval, or other shape. Annular ultrasound transducer arrays may be utilized. The various shapes, forms, and configurations of two-dimensional ultrasound arrays, and associated beam-forming techniques are well-known and may be implemented in various embodiments of the optical-acoustic diagnostic apparatus 100.

Figure 6A:
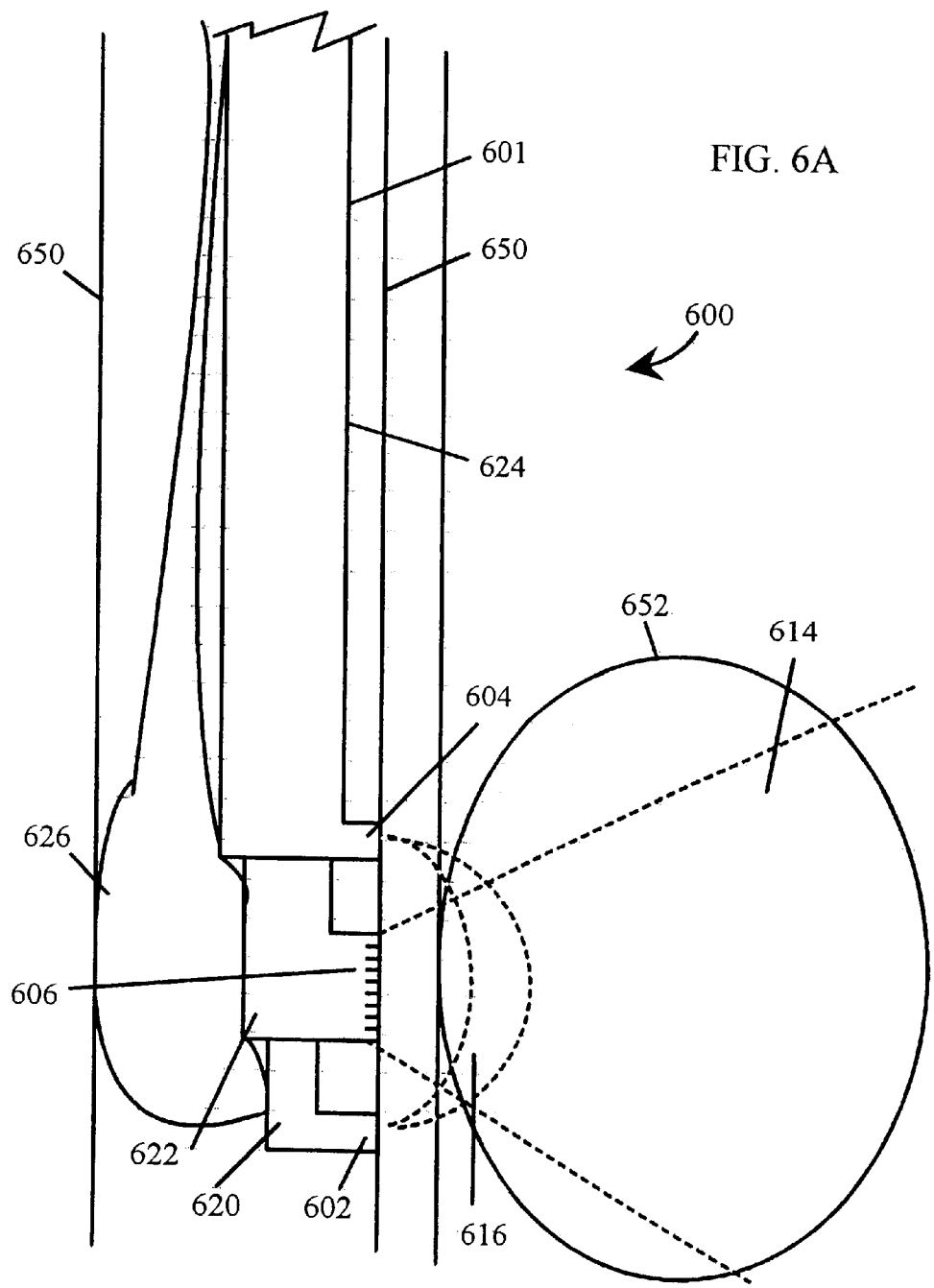
FIGS. 6A and 6B are schematic pictorial diagrams that illustrate examples of a combined optical-acoustic diagnostic apparatus in a catheter oxygenation probe configuration.

Referring to FIG. 6A, a schematic pictorial diagram illustrates an example of a combined optical-acoustic diagnostic apparatus 600, which may also be called a probe, in a catheter oxygenation probe configuration. Combined optical-acoustic diagnostic apparatus 600 is an example of a near infrared spectrophotometer (NIRS) that is useful for tissue oxygenation monitoring. The ultrasound guided optical-acoustic diagnostic apparatus 600 has a fixture 601 that holds an optical source 602, an optical detector 604, and an ultrasound transducer 606 in a single plane. In that single plane, the optical source 602, the optical detector 604, and the ultrasound transducer 606 are distributed in a line with the ultrasound transducer 606 between the optical source 602 and the optical detector 604. In the described arrangement, the optical source 602 and optical detector 604 generate an optical sample volume 616 that intersects an ultrasound sample volume 614 formed by the ultrasound transducer 606. The ultrasound sample volume 614 is typically interrogated by ultrasound imaging to produce a multi-dimensional ultrasound image. In contrast, the optical sample volume 616 depicts diagnostic characteristics of tissue in a pathway between the optical source 602 and detector 604 that can be positioned within the ultrasound image.

The ultrasound guided NIRS system is capable of monitoring fetal oxygenation and fetal heart rate during labor and delivery. In addition, a typical ultrasound guided NIRS embodiment is substantially noninvasive, utilizes nonionizing energy, and can be used at the bedside because the size and form factor are the same as a diagnostic ultrasound imager. The ultrasound guided NIRS can provide continuous tissue oxygenation measurements at the same rate as the heart rate. Ultrasound guided NIRS can have low cost because of utilization of semiconductor laser diodes for the optical source. Ultrasound guided NIRS does not require fragile fiber optic cables to transmit and receive the light and thus is highly reliable.

In some embodiments, the fixture 601 comprises three concentrically-arranged catheters, for example arranged in a telescopic configuration. For example, an optical source catheter 620 is connected to the optical source 602 and is enclosed within a larger ultrasound transducer catheter 622. The ultrasound transducer catheter 622 is connected to the ultrasound transducer 606 and is enclosed within a larger optical detector catheter 624. The optical source catheter 620 extends from the ultrasound transducer catheter 622 that extends from the optical detector catheter 624. Alternatively, the fixture 601 can be arranged so that the optical source 602 and the optical detector 604 are interchanged.

The catheter optical-acoustic diagnostic apparatus 600 may further comprise an inflatable balloon 626 that, when inflated, holds the fixture 601 against an organ wall 650 to enable diagnostic measurements of different tissues 652. The optical-acoustic diagnostic apparatus 600 is a probe that can be inserted into a cavity or vessel, such as the esophagus, artery, vein, rectum, nasal passages and the like, and held against the organ wall 650 with the inflatable balloon 626. The optical source catheter 620, the ultrasound transducer catheter 622, and the optical detector catheter 624 can be extended or retracted mutually independently allowing for a variable source-photodetector distance and variable centering of the ultrasound transducer 606. A position detector (not shown) detects relative positioning of the catheter.

The catheter optical-acoustic diagnostic apparatus 600 can be used for many functions. In one example, the catheter optical-acoustic diagnostic apparatus 600 can be used for determining myocardial oxygenation in heart monitoring. A clinician can rotate, extend, or retract the ultrasound transducer array catheter 622 to position the ultrasound sample volume 614 in a selected tissue field in the myocardium. The clinician can extend or retract either or both the optical source catheter 620 and optical detector catheter 624 to position the optical sample volume outline through the myocardium on an electronic display. The clinician can inflate the inflatable balloon 626 to hold the optical-acoustic probe 600 in position. The clinician can activate the optical-acoustic probe 600 to continuously measure tissue oxygenation using near infrared spectrometry (NIRS).

In some embodiments, the catheter optical-acoustic diagnostic apparatus 600 may be used for intrauterine fetal monitoring and include an annunciator (not shown) and trigger (not shown) that operate in combination to generate an annunciator signal when the tissue oxygenation level has reached a threshold. A clinician can respond to the annunciator signal by beginning appropriate procedures.

Figure 6B:
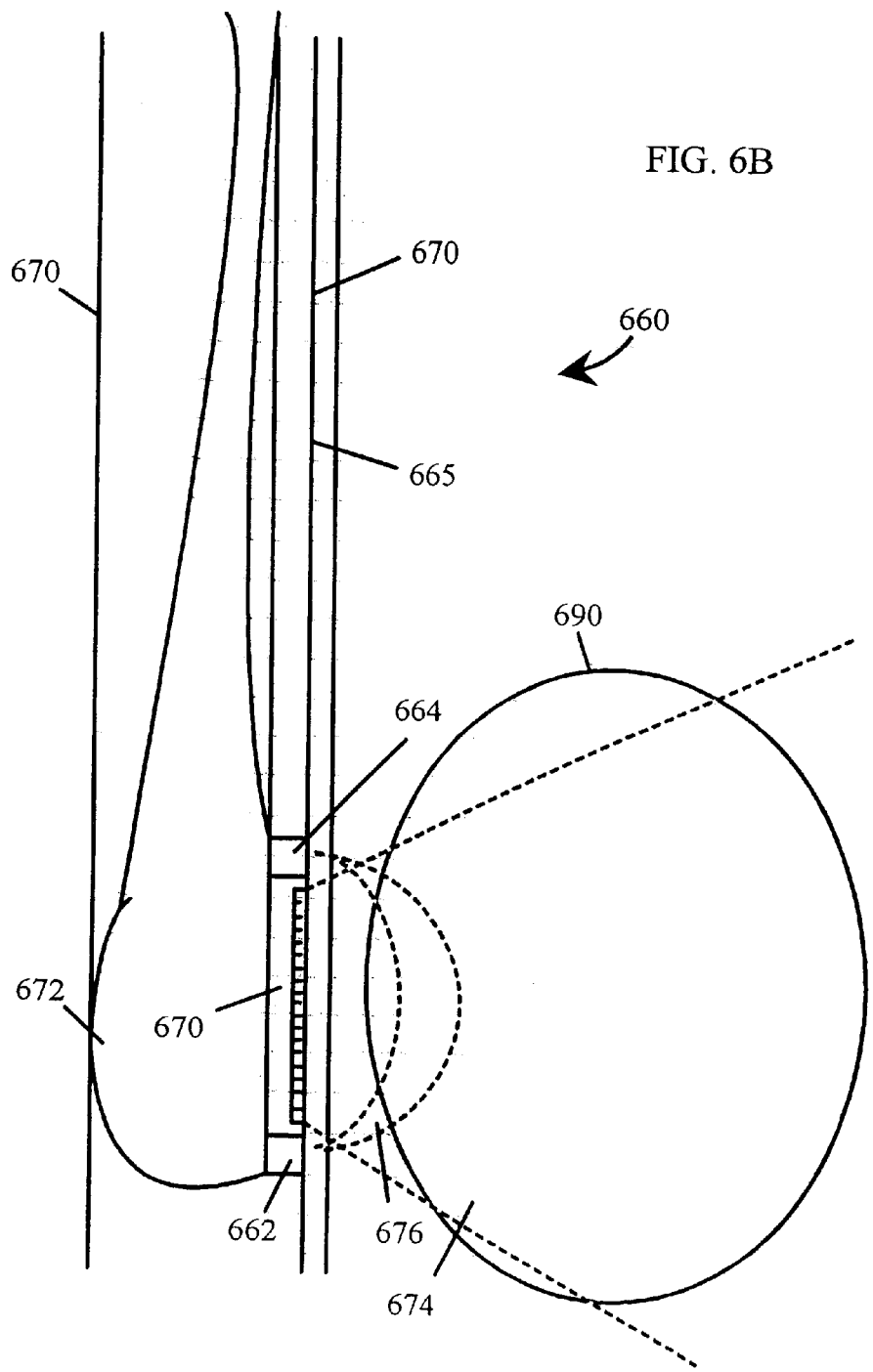

Referring to FIG. 6B, a schematic pictorial diagram illustrates an alternative embodiment of a combined optical-acoustic diagnostic apparatus 660 in a catheter oxygenation probe configuration, a catheter near infrared spectrophotometer (NIRS) that is useful for myocardium oxygenation monitoring. The catheter optical-acoustic diagnostic apparatus 660 has a catheter 665 that holds an optical source 662, an optical detector 664, and an ultrasound transducer 670 in a single plane. In that single plane, the optical source 662, the optical detector 664, and the ultrasound transducer 670 are distributed in a line with the ultrasound transducer 670 between the optical source 662 and the optical detector 664. In the described arrangement, the optical source 662 and optical detector 664 generate an optical sample volume 676 that intersects an ultrasound sample volume 674 formed by the ultrasound transducer 670. The ultrasound sample volume 674 is typically interrogated by ultrasound imaging to produce a multi-dimensional ultrasound image. In contrast, the optical sample volume 676 depicts diagnostic characteristics of tissue in a pathway between the optical source 662 and detector 664 that can be positioned within the ultrasound image.

In some embodiments, the catheter 665 contains any signal conductive elements for driving signals to the optical source 662 and elements of the ultrasound transducer 670 and sensing signals received from the ultrasound transducer elements and the optical detector 664. Typical signal conductive elements may be optical or electric transmission lines. The catheter 665 can be arranged so that the optical source 662, the optical detector 664, and the ultrasound transducer elements are in any suitable order.

The catheter optical-acoustic diagnostic apparatus 660 may further comprise an inflatable balloon 672 that, when inflated, holds the catheter 665 against an organ or tissue wall 670 to enable diagnostic measurements within the tissue 690. In one example, the catheter optical-acoustic diagnostic apparatus 660 is a probe that can be inserted into a patient's esophagus and held against the esophageal wall 670 with the inflatable balloon 672. The source-photodetector distance and centering of the ultrasound transducer 670 are fixed in the illustrative catheter 665.

Figure 7:
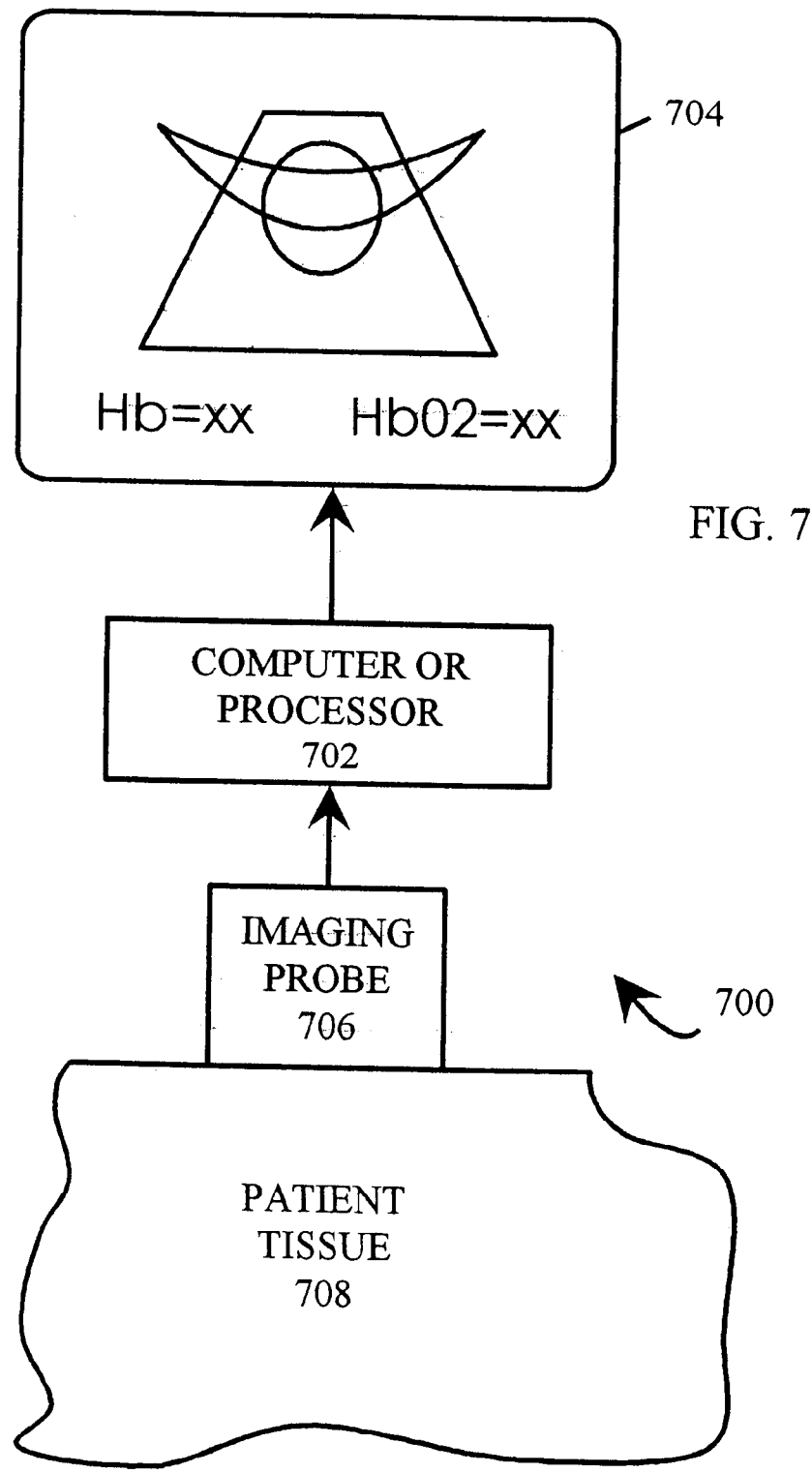
FIG. 7 is a schematic block diagram showing an example of a combined optical-acoustic diagnostic apparatus including processor and display.

Referring to FIG. 7, a schematic block diagram shows an example of a combined optical-acoustic diagnostic apparatus 700 including processor 702 and electronic display 704. The processor 702 can be any type of general-purpose or special-purpose processor or computer such as a microprocessor, microcontroller, central processing unit, programmable control logic, state machine, or the like. The electronic display 704 is any suitable general-purpose or special-purpose display device, such as an electronic graphics display.

The optical-acoustic diagnostic apparatus 700 also includes an optical-acoustic imaging probe 706. Examples of the optical-acoustic imaging probe 706 include the trans-abdominal fetal oxygenation probe 100, the catheter optical-acoustic diagnostic apparatus 600, or other optical-acoustic device that includes an optical source and detector, and an ultrasound transducer, as described hereinbefore.

The electronic display 704 can present a two-dimensional ultrasound image of the structure of imaged anatomy. Typically, the processor 702 can calculate a theoretical optical sample volume based on source-photodetector distance and optical properties of patient tissues 708 in the optical sample volume. The processor 702 superimposes a portion of the optical sample volume that intersects the ultrasound sample volume over the ultrasound image. The optical sample volume outline can be represented by either dotted lines or shading.

In operation, a clinician may first manipulate the ultrasound transducer so the ultrasound image passes through target tissue for performing an oxygenation measurement. The clinician either may increase or decrease the optical source-photodetector distance to position the optical sample volume outline through the tissue of interest. Increasing the source-photodetector distance results in a deeper optical sample volume outline. Decreasing the source-photodetector distance results in a shallower optical sample volume outline. The clinician then initiates a near infrared spectrometry (NIRS) oxygenation measurement of the tissue of interest.

Figure 8:
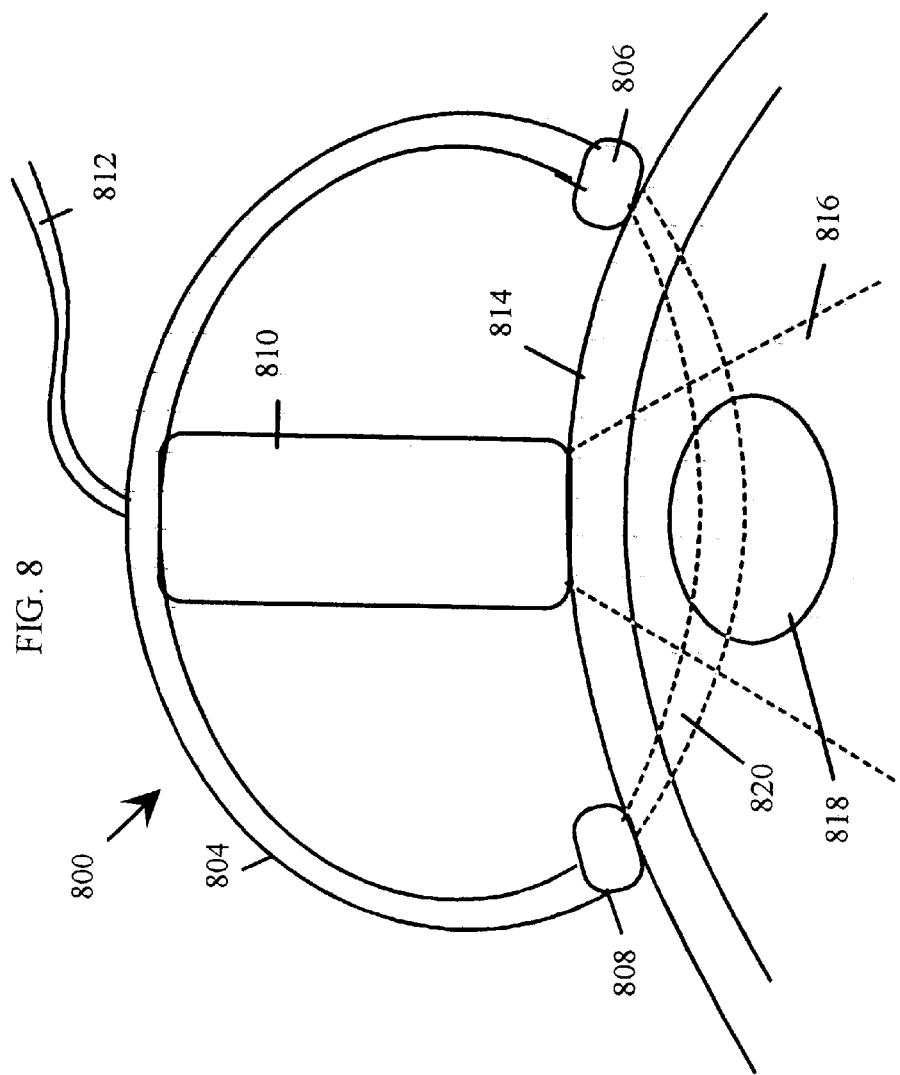
FIG. 8 is a representative pictorial diagram depicting a fetal brain oxygenation test configuration, an example of a clinical application of a combined optical-acoustic diagnostic apparatus.

Referring to FIG. 8, a representative pictorial diagram depicts an example of a fetal brain oxygenation test configuration 800 including an optical-acoustic probe 802 held by a stereotaxic holder 804. The optical-acoustic probe 802 includes an optical source 806, optical photodetector 808, and ultrasound transducer 810. A cable 812 connects the optical-acoustic probe 802 to an imaging system.

A clinician places the trans-abdominal fetal oxygenation probe 802 in contact with a patient's skin 814 in the vicinity of the mother's abdomen. The clinician manipulates the trans-abdominal oxygenation probe 802 to position the ultrasound sample volume 816 through the center of the fetal skull 818 by viewing an ultrasound image acquired by usage of the ultrasound transducer 810 on an electronic display. The clinician increases or decreases the optical source-photodetector distance to position the optical sample volume outline through the center of the fetal skull on the electronic display. Once the optical sample volume 820 is positioned, the clinician can acquire a measurement of hemoglobin (Hb) and oxyhemoglobin (HbO2) is taken with near infrared spectrometry (NIRS).

The optical-acoustic probe 802 can be used to image any deep tissue, organs, a fetus in a maternal condition, and the like.

Biological tissue varies in index of refraction and optical properties among different tissues in one person and among different individual persons. The shape and position of an optical sample volume varies based on the refraction index and optical properties so that calibration is generally useful to produce accurate measurements. "Phantoms" are test fixtures composed materials with the optical properties that are equivalent or approximately equivalent to trans-abdominal, trans-esophageal, or other desired target tissues. Phantoms typically mimic oxygenation characteristics of actual biological tissue. The tissue phantoms can be used to determine the shape and position of the optical sample volume for a specific source-photodetector distance.

Figure 9:
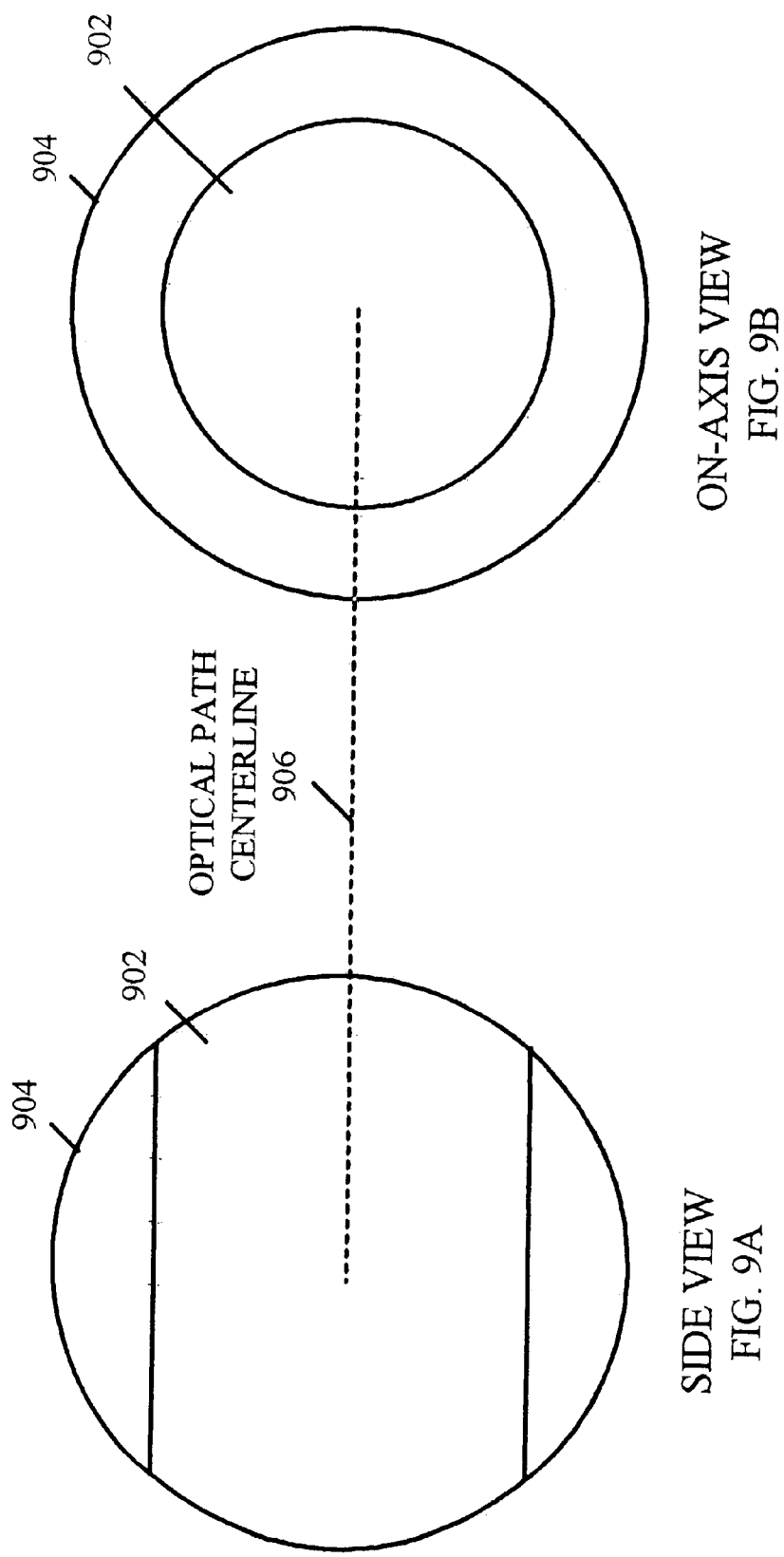
FIGS. 9A and 9B are pictorial diagrams that show side and on-axis views of an example of a trans-abdominal fetal tissue calibration phantom or fixture.

Referring to FIGS. 9A and 9B, pictorial diagrams show side and on-axis views of an example of a trans-abdominal fetal tissue calibration phantom or fixture 900. The illustrative trans-abdominal fetal tissue calibration phantom 900 has a spherical shape although other shapes including oval, oblong, cylindrical, or other shapes may be used. The illustrative trans-abdominal fetal tissue calibration phantom 900 has two regions containing material with different absorption characteristics, although other phantoms may include more or fewer regions. The illustrative trans-abdominal fetal tissue calibration phantom 900 includes an inner vesicle 902 containing a low absorptive material and an outer region 904 containing a high absorptive material. The low absorptive material and the high absorptive material approximate characteristics of biological tissue.

During measurements of actual biological tissue, photons emitted from the optical source pass through the abdominal wall, amniotic fluid, fetal brain, amniotic fluid, and the abdominal wall layers. Components of the tissue phantom have similar optical properties of absorption, scattering and index of refraction in comparison to actual tissue except for the fetal brain sphere. The fetal brain sphere has a cylinder of low absorptive material surrounded by high absorptive material. The trans-abdominal fetal tissue calibration phantom 900 includes the inner vesicle 902 that approximates characteristics of the fetal brain sphere. The trans-abdominal fetal tissue calibration phantom 900 includes the outer region 904 that approximates characteristics of the abdominal wall and the amniotic fluid. A centerline 906 of the inner vesicle cylinder 902 is parallel to the optical path of the photons at the deepest point of the sample volume.

The optical-acoustic diagnostic apparatus is calibrated by determining the source-photodetector distance where the optical sample volume is positioned in the low absorption cylinder of the brain sphere. The source-photodetector distance that results in the optical sample volume being positioned in the low absorptive cylinder of the brain sphere is experimentally determined. The calibration procedure begins with a very short source-photodetector distance. The photodetector signal is low as the beam passes completely through the abdominal wall layer and increases through the amniotic fluid layer. The photodetector signal then decreases as the beam passes through the high absorptive section of the fetal brain sphere and increases as the beam continues through the low absorptive center cylinder of the fetal brain sphere. The photodetector signal decreases as the beam passes through the deeper high absorptive section of the fetal brain sphere.

Figure 10:
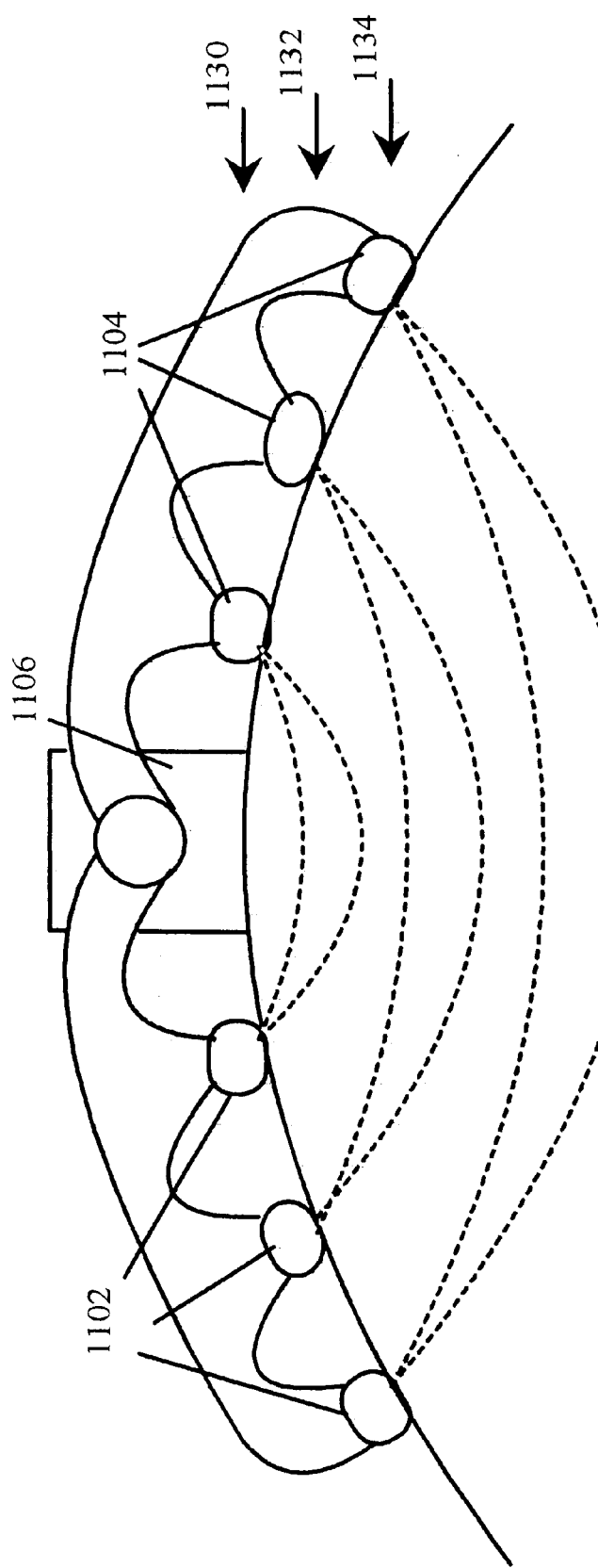
FIGS. 10 and 11 are schematic pictorial diagrams that depict a side view of other examples of a combined optical-acoustic diagnostic apparatus with multiple sets of optical sources and optical detectors.

Referring to FIG. 10, a pictorial diagram illustrates an example of a trans-esophageal myocardium tissue phantom 1000. The illustrative trans-esophageal myocardium tissue phantom 1000 includes a plurality of layers of material having predetermine optical absorption characteristics. Typically the layers are in the form of rectangular blocks of like length and width, and selected thickness', which are typically variable to simulate the thickness of various biological tissues. The geometry and structure of the layers may be selected to suitably match a particular tissue for a desired application. For example, the sizes may differ for embodiments that simulate tissue other than trans-esophageal myocardium.

The illustrative trans-esophageal myocardium tissue phantom 1000 has an esophageal wall layer 1002 on an outer surface 1004, an outer heart layer 1006 coupled to the esophageal wall layer 1002, and a myocardium layer 1008 coupled to the outer heart layer 1006. An inner heart wall layer 1010 is coupled to the myocardium layer 1008. In some embodiments, a heart chamber layer 1012 may be coupled to the inner heart wall layer 1010. In one example, the esophageal wall layer 1002 is 2 mm thick and has a medium absorption characteristic. The outer heart layer 1006 is 1 mm thick and also has a medium absorption characteristic that is typically different from the absorption characteristic of the esophageal wall layer 1002. The myocardium layer 1008 is 1 to 2 cm thick and typically has a low absorption characteristic. The inner heart wall layer 1010 is 1 cm thick and has a high absorption characteristic. A typical low absorption characteristic has a range from 0 to 0.006 $mm^{-1}$. A typical medium absorption characteristic has a range from 0.006 to 0.016 $mm^{-}$. A typical high absorption characteristic has a range from 0.016 to a maximum of approximately 0.04 $mm^{-1}$.

A source-photodetector distance that positions the optical sample volume in the center of the myocardium layer is experimentally determined. For a short source-photodetector distance, the optical sample volume only passes through the medium absorption of the esophageal wall 1002 and outer wall of the heart 1006. As the source-photodetector distance increases, absorption decreases because the absorption of photons is increased due to the longer path length. The source-photodetector distance is increased until the increase in absorbance of the inner wall 1010 is detected. The ratio of source-photodetector distance to myocardium depth is computed and used to display the optical sample volume outline.

Referring to FIG. 10, a schematic pictorial diagram depicts a side view of another example of a combined optical-acoustic diagnostic apparatus 1100 having multiple sets of optical source-detectors 1130, 1132, and 1134, and an ultrasound transducer 1106. The multiple optical source-detectors 1130, 1132, and 1132 of the illustrative optical-acoustic diagnostic apparatus 1100 each include a plurality of optical sources 1102 and detector 1104. The multiple optical source-detectors 1130, 1132, and 1132 are connected to lateral members 1108 or arms that separate the respective optical sources 1102 and detectors 1104. The optical source-detectors 1130, 1132, and 1132 each generate separate optical sample volumes that are positioned in different portions of tissue, and that intersect the ultrasound sample volume. Although the illustrative optical-acoustic diagnostic apparatus 1100 includes three sets of optical source-detectors 1130, 1132, and 1132, any suitable number may be utilized so long as the optical sources 1102, optical detectors 1104, and ultrasound transducer 1106 are in the same plane so that all optical sample volumes intersect the ultrasound sample volume. In other embodiments, multiple ultrasound transducers may be used.

Figure 11:
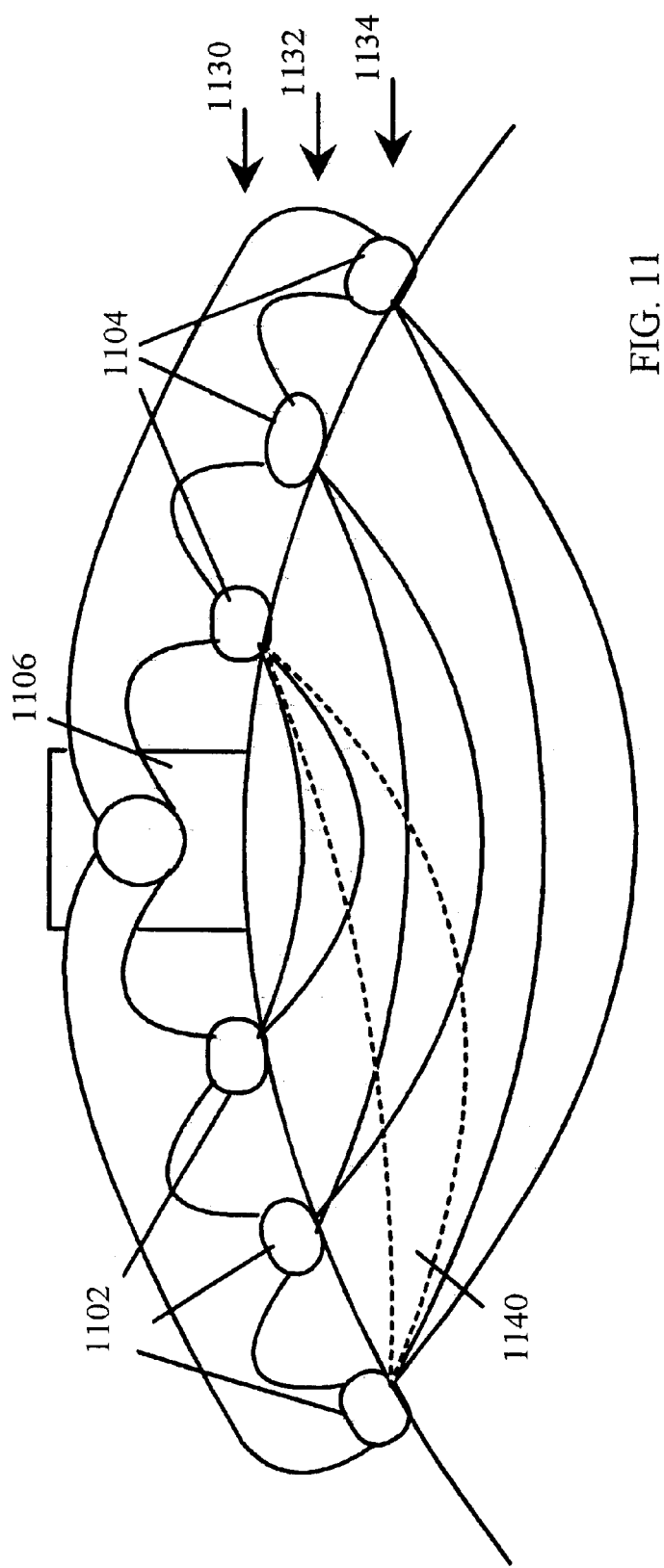

Additional volumes may be imaged as shown in FIG. 11 by detecting light emitted from various sources. For example, dashed lines show the optical volume 1140 generated by source 1134 and detector 1130. Similarly, any of the detectors sense light emitted by any of the sources. Different optical samples can be generated, for example simply by correlating the timing of emission by the different sources and the detection by the different detectors.

Figure 12:
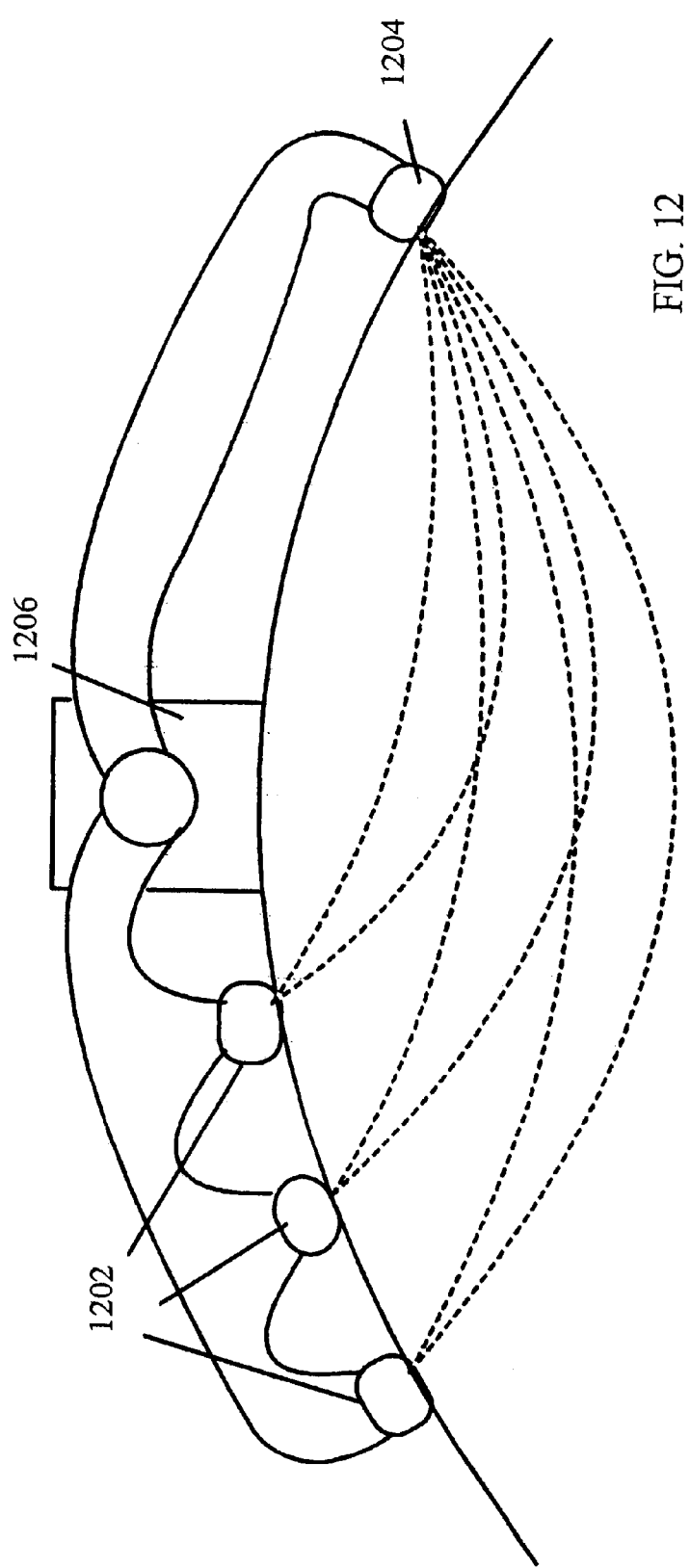
FIG. 12 is a schematic pictorial diagram depicts a side view of another example of a combined optical-acoustic diagnostic apparatus having a plurality of optical sources and a plurality of optical detectors with the number of optical sources being different from the number of optical detectors.

Referring to FIG. 12, a schematic pictorial diagram depicts a side view of another example of a combined optical-acoustic diagnostic apparatus 1200 having a plurality of optical sources 1202 and a plurality of optical detectors 1204 with the number of optical sources 1202 being different from the number of optical detectors 1204. The multiple optical sources 1202 and optical detectors 1204 are connected to lateral members 1208 or arms that separate the respective optical sources 1202 and detectors 1204. The optical sources 1202 and optical detectors 1204 generate separate optical sample volumes that are positioned in different portions of tissue, and that intersect the ultrasound sample volume. Although the illustrative optical-acoustic diagnostic apparatus 1200 includes a single optical source 1202 and three optical detectors 1204, any suitable number may be utilized so long as the optical sources 1202, optical detectors 1204, and ultrasound transducer 1206 are in the same plane so that all optical sample volumes intersect the ultrasound sample volume. In other embodiments, multiple ultrasound transducers may be used.

While the invention has been described with reference to various embodiments, it will be understood that these embodiments are illustrative and that the scope of the invention is not limited to them. Many variations, modifications, additions and improvements of the embodiments described are possible. For example, those skilled in the art will readily implement the steps necessary to provide the structures and methods disclosed herein, and will understand that the process parameters, materials, and dimensions are given by way of example only and can be varied to achieve the desired structure as well as modifications which are within the scope of the invention. Variations and modifications of the embodiments disclosed herein may be made based on the description set forth herein, without departing from the scope and spirit of the invention as set forth in the following claims.

In the claims, unless otherwise indicated the article "a" is to refer to "one or more than one".

What is claimed is:

1. A diagnostic apparatus comprising:

a near infrared spectrophotometer comprising one or more optical sources and one or more optical detectors capable of interrogating one or more optical source volumes;

an ultrasound transducer capable of interrogating an ultrasound source volume, the optical sources, the optical detectors, and the ultrasound transducer being configured in a line so that the one or more optical source volumes and the ultrasound source volume are coplanar and the one or more optical source volumes intersect the ultrasound source volume; and a moveable fixture coupled to the one or more optical sources, the one or more optical detectors, and the ultrasound transducer, and capable of adjustment to vary optical source-detector distances of respective one or more optical sources and one or more optical detectors.

2. A diagnostic apparatus according to claim 1 wherein:
the moveable fixture is capable of adjustment to vary distances between the ultrasound transducer and the one or more optical sources and the one or more optical detectors.

3. A diagnostic apparatus according to claim 2 further comprising:
a detector coupled to the moveable fixture and capable of detecting one or more of the position of one or more of the optical sources, one or more of the optical detectors, and the ultrasound transducer; and
a processor coupled to the detector and capable of determining a source-detector distance based on the one or more positions.

4. A diagnostic apparatus according to claim 1 wherein:
an optical source of the one or more optical sources and a corresponding optical detector of the one or more optical detectors comprise a near infrared spectrophotometer that is capable of determining optical properties of tissue in the optical sample volume.

5. A diagnostic apparatus according to claim 4 wherein the near infrared spectrophotometer is an absorption spectroscopy device that comprises:
an optical source capable of being positioned on a tissue and emitting infrared light into the tissue at a plurality of selected wavelengths; and
a photodetector capable of detecting the selected wavelengths of light from the tissue, the photodetector being positioned on the tissue removed from the optical source but sufficiently close in proximity to the optical source to contact the same general tissue,
the near infrared spectrophotometer being capable of detecting measurable changes in absorbance of a plurality of wavelengths of analytes of interest within the tissue.

6. A diagnostic apparatus according to claim 4 wherein the near infrared spectrophotometer is an intensity modulation spectroscopy device that comprises:
an optical source capable of being positioned on a tissue and emitting infrared light into the tissue at a plurality of selected wavelengths;
a photodetector capable of detecting the selected wavelengths of light from the tissue, the photodetector being positioned on the tissue removed from the optical source but sufficiently close in proximity to the optical source to contact the same general tissue; and
an oscillator coupled to the optical source and providing intensity modulation controlling the optical source, the optical source being responsive to the modulation by emitting the plurality of selected wavelengths, the selected wavelengths being selected to generate measurable changes in absorbance of analytes of interest within the tissue.

7. A diagnostic apparatus according to claim 4 wherein the near infrared spectrophotometer is a differential spectroscopy device that comprises:
an optical source capable of being positioned on a tissue and emitting infrared light into the tissue at a plurality of selected wavelengths; and
a photodetector capable of detecting the selected wavelengths of light from the tissue, the photodetector being positioned on the tissue removed from the optical source but sufficiently close in proximity to the optical source to contact the same general tissue,
the near infrared spectrophotometer being capable of producing a wavelength shift of a plurality of wavelengths to generate measurable changes in absorbance of analytes of interest within the tissue.

8. A diagnostic apparatus according to claim 1 further comprising:
an trigger capable of detecting a preselected oxygenation level; and
an annunciator capable of generating a warning signal when the trigger detects the preselected oxygenation level.

9. A diagnostic apparatus according to claim 1 further comprising:
a catheter coupled to the one or more optical sources, the one or more optical detectors, and the ultrasound transducer.

10. A diagnostic apparatus comprising:
a near infrared spectrophotometer comprising one or more optical sources and one or more optical detectors capable of interrogating one or more optical source volumes;
an ultrasound transducer capable of interrogating an ultrasound source volume, the optical sources, the optical detectors, and the ultrasound transducer being configured in a line so that the one or more optical source volumes and the ultrasound source volume are coplanar and the one or more optical source volumes intersect the ultrasound source volume;
first and second lateral members coupled respectively to the one or more optical sources and to the one or more optical detectors;
a pivot coupling the first and second lateral members; and
position detectors for determining a relative angle between the ultrasound transducer and one or more optical sources, and a relative angle between the ultrasound transducer and the one or more optical detectors.

11. A diagnostic apparatus comprising:
a near infrared spectrophotometer comprising one or more optical sources and one or more optical detectors capable of interrogating one or more optical source volumes;
an ultrasound transducer capable of interrogating an ultrasound source volume, the optical sources, the optical detectors, and the ultrasound transducer being configured in a line so that the one or more optical source volumes and the ultrasound source volume are coplanar and the one or more optical source volumes the ultrasound source volume;
a plurality of concentrically-arranged catheters in a telescopic configuration; and position detectors for determining relative positioning of the plurality of catheters.

12. A diagnostic apparatus according to claim 11 wherein:
the optical sources, the optical detectors, and thie ultrasound transducer are mounted on one or more of the plurality of concentrically-arranged catheters.

13. A diagnostic apparatus comprising:
a near infrared spectrophotometer comprising one or more optical sources and one or more optical detectors capable of interrogating one or more optical source volumes;
an ultrasound transducer capable of interrogating an ultrasound source volume, the optical sources, the optical detectors, and the ultrasound transducer being configured in a line so that the one or more optical source volumes and the ultrasound source volume are coplanar and the one or more optical source volumes intersect the ultrasound source volume;

a first lateral member coupled to the one or more optical sources;

a second lateral member coupled to the one or more optical detectors, the ultrasound transducer being coupled to the first lateral member and the second lateral member;

one or more position sensors for detecting an angle between the first lateral member and the ultrasound transducer, and for detecting an angle between the second lateral member and the ultrasound transducer; and a processor coupled to the one or more position sensors and capable of determining a source-detector distance.

14. A diagnostic apparatus according to claim 13 further comprising:

a display, the processor being capable of controlling the display to display an image of the ultrasound sample volume and to display an image of the optical sample volume relative to the ultrasound sample volume image as a function of the source-detector distance and optical properties of interrogated tissue.

15. A diagnostic apparatus comprising:

a near infrared spectrophotometer comprising one or more optical sources and one or more optical detectors capable of interrogating one or more optical source volumes;

an ultrasound transducer capable of interogating an ultrasound source volume, the optical sources, the optical detectors, and the ultrasound transducer being configured in a line so that the one or more optical source volumes and the ultrasound source volume are coplanar and the one or more optical source volumes intersect the ultrasound source volume;

a fixture for holding one or more optical sources, the one or more optical detectors, and the ultrasound transducer, the fixture including a plurality of catheters, one or more position sensors coupled to the plurality of catheters; and a processor coupled to the one or more position sensors and capable of determining a source-detector distance.

16. A diagnostic apparatus according to claim 15 further comprising:

a display, the processor being capable of controlling the display to display an image of the ultrasound sample volume and to display an image of the optical sample volume relative to the ultrasound sample volume image as a function of the source-detector distance and optical properties of interrogated tissue.

17. A diagnostic apparatus according to claim 15 wherein:

the fixture is configured to extend, retract, and rotate the optical sources, optical detectors, and ultrasound transducer.

18. A diagnostic apparatus according to claim 15 further comprising:

a balloon capable of inflation for securing the optical source, the optical detector, and the ultrasound transducer against tissue.

19. A diagnostic apparatus comprising:

at least one optical source;

at least one optical detector;

at least one ultrasound transducer;

a first lateral member coupled to the at least one optical source;

a second lateral member coupled to the at least one optical detector, the at least one ultrasound transducer being coupled to the first lateral member and the second lateral member;

at least one position sensor for detecting an angle between the first lateral member and the at least one ultrasound transducer, and for detecting an angle between the second lateral member and the at least one ultrasound transducer; and a processor coupled to the at least one position sensor and capable of determining a source-detector distance, the first and second lateral members, the at least one optical source, the at least one optical detector, and the at least one ultrasound transducer being configured for determining fetal brain oxygenation.

20. A diagnostic apparatus according to claim 19 further comprising:

a display, the processor being capable of controlling the display to display an image of the ultrasound sample volume and to display an image of the optical sample volume relative to the ultrasound sample volume image as a function of the source-detector distance and optical properties of interrogated tissue.

21. A diagnostic apparatus comprising:

one or more optical sources;

one or more optical detectors;

an ultrasound transducer;

a fixture for holding the one or more optical sources, the one or more optical detectors, and the ultrasound transducer, the fixture including a plurality of catheters;

one or more position sensors coupled to the plurality of catheters; and a processor coupled to the one or more position sensors and capable of determining a source-detector distance, the fixture, optical source, optical detector, and ultrasound transducer being configured for determining tissue oxygenation.

22. A diagnostic apparatus according to claim 21 further comprising:

a display, the processor being capable of controlling the display to display an image of an ultrasound sample volume and to display an image of an optical sample volume relative to the ultrasound sample volume image as a function of the source-detector distance and optical properties of interrogated tissue.

23. A diagnostic apparatus according to claim 21 wherein:

the fixture is configured to extend, retract, and rotate the optical sources, optical detectors, and ultrasound transducer.

24. A diagnostic apparatus according to claim 21 further comprising:

a balloon capable of inflation for securing the optical source, the optical detector, and the ultrasound transducer against tissue.

25. A diagnostic apparatus according to claim 21 further comprising;

an trigger capable of detecting a preselected oxygenation level; and an annunciator capable of generating a warning signal when the trigger detects the preselected oxygenation level.

* * * * *